US012746333B2

(12) United States Patent
Cho et al.

(10) Patent No.: US 12,746,333 B2
(45) Date of Patent: Sep. 29, 2026

(54) MULTI-COMPARTMENT SYRINGE WITH PUMP MECHANISM

(71) Applicant: Regents of the University of Minnesota, Minneapolis, MN (US)

(72) Inventors: Roy Joseph Cho, Minneapolis, MN (US); Felix Landaeta, Minneapolis, MN (US); Matthew Kudek, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1170 days.

(21) Appl. No.: 15/733,552

(22) PCT Filed: Feb. 28, 2019

(86) PCT No.: PCT/US2019/020081

§ 371 (c)(1),
(2) Date: Aug. 26, 2020

(87) PCT Pub. No.: WO2019/169151

PCT Pub. Date: Sep. 6, 2019

(65) Prior Publication Data

US 2020/0397990 A1 Dec. 24, 2020

Related U.S. Application Data

(60) Provisional application No. 62/636,535, filed on Feb. 28, 2018.

(51) Int. Cl.
*A61B 10/02* (2006.01)
*A61B 10/04* (2006.01)
(Continued)

(52) U.S. Cl.
CPC ........... *A61M 5/19* (2013.01); *A61B 10/0283* (2013.01); *A61B 2010/045* (2013.01); *A61M 2005/3128* (2013.01)

(58) Field of Classification Search
CPC ............ A61M 5/19; A61M 2005/3128; A61M 39/223; A61M 5/001; A61M 2005/005;
(Continued)

(56) References Cited

U.S. PATENT DOCUMENTS

2008/0221480 A1 9/2008 Hibner
2009/0131817 A1 5/2009 Speeg
(Continued)

OTHER PUBLICATIONS

International Preliminary Report on Patentability for International Application No. PCT/US2019/020081, dated Sep. 1, 2020, 7 pages.
(Continued)

*Primary Examiner* — Kevin C Sirmons
*Assistant Examiner* — William R Frehe
(74) *Attorney, Agent, or Firm* — Husch Blackwell LLP

(57) ABSTRACT

Disclosed herein are various embodiments of a multi-chamber syringe module for use in fine needle aspiration or other procedures. The multi-chamber syringe module includes a multi-chamber cartridge. The multi-chamber cartridge can include a plurality of fluid chambers. The multi-chamber syringe module also includes a needle manifold that is rotatably coupled to the multi-chamber cartridge. The multi-chamber syringe module further includes a luer fitting hub fixedly coupled to the needle manifold at a first end and selectively coupled to a biopsy needle at a second end.

9 Claims, 23 Drawing Sheets

(51) Int. Cl.
*A61M 5/19* (2006.01)
*A61M 5/31* (2006.01)

(58) Field of Classification Search
CPC .......... A61B 10/0283; A61B 2010/045; A61B 10/0096; A61B 2010/0225; A61B 2010/0208
See application file for complete search history.

(56) References Cited

U.S. PATENT DOCUMENTS

| | | | | |
|---|---|---|---|---|
| 2010/0113973 | A1* | 5/2010 | Hibner | A61B 10/0275 600/567 |
| 2016/0183928 | A1* | 6/2016 | Speeg | A61B 10/02 600/562 |
| 2018/0049729 | A1* | 2/2018 | Sullivan | A61B 10/0283 |

OTHER PUBLICATIONS

International Search Report and Written Opinion for International Application No. PCT/US2019/020081, dated Sep. 1, 2020, 8 pages.

* cited by examiner

MULTI-COMPARTMENT SYRINGE WITH PUMP MECHANISM

RELATED APPLICATION

The present application is a National Phase entry of PCT Application No. PCT/US2019/020081, filed Feb. 28, 2019, which claims priority from U.S. Provisional Application No. 62/636,535 filed Feb. 28, 2018, which is hereby incorporated herein in its entirety by reference.

TECHNICAL FIELD

This disclosure relates generally to a syringe device, and more particularly to a multi-chamber syringe for use with a biopsy needle.

BACKGROUND

Endoscopic fine needle aspiration (hereinafter "FNA") is a widely practiced procedure in the United States and worldwide. FNA is commonly used for the diagnosis of cancer, in particular lung and gastrointestinal. Conventionally, FNA is performed using a needle, two syringes and a vacuum-assisted syringe device. For lung cancer, the FNA needle is used in combination with a bronchoscope.

Conventionally, FNA begins with identifying a target tissue. A target tissue can be a lymph node, nodule, or mass that a medical professional has determined suspect and requires a biopsy. Once a target tissue is identified, conventionally by ultrasound or by electromagnetic navigational bronchoscopy (hereinafter "ENB"), a needle is inserted into the target tissue. The needle is then agitated by an operator using a back-and-forth motion, while under vacuum. The vacuum is conventionally created via syringe suction. Once the needle is retracted with a tissue specimen, the needle portion is removed from the bronchoscope and the tissue specimen is aspirated from the needle into a container and ultimately onto glass slides for analysis. During aspiration, two syringes are filled: one syringe is filled with a saline solution, and one syringe is filled with air. The saline-filled syringe is coupled to the needle portion containing the target tissue, and the saline can be used to ejects the target tissue through the needle by compressing a plunger of the syringe. Then, the air-filled syringe is coupled to the needle portion containing the target tissue, and the air can be used to clean out any sample or saline solution remaining in the needle by compressing a plunger of the syringe. The needle portion is then reattached to the bronchoscope and a new FNA process can begin again.

Thus, for each procedure, a total of three syringes are used. First, a syringe is attached to the back of the FNA needle and pulled open and locked to create the vacuum that is used to draw the sample to be tested. Once the sample has been pulled into the needle by this vacuum, the syringe must be detatched and a second needle filled with saline must be attached in order to deposit the collected sample into a container for analysis. Third, a syringe filled with air must be attached in order to clean out the needle.

In a typical procedure, an FNA process can be repeated multiple times (referred to as "passes"), with ten or more passes used in some cases in order to guarantee sufficient quantities of a sample are collected. Thus the total number of syringes that must be attached and detatched can be about 30 per patient. A surgeon conducting FNA procedures typically performs up to five or six procedures per day, resulting in the need to attach and detatch as many as 180 syringes in precise order each day.

The attachment and reattachment adds time to each FNA procedure. Furthermore, surgeons who are focused on the attachment or detachment of syringes are not focused on the procedure, and have reduced attention to provide to the patient during those times.

SUMMARY

Various embodiments of a multi-chamber syringe module for use with a biopsy needle in Fine Needle Aspiration (FNA), gastrointestinal treatments such as colonoscopies, or other procedures, are disclosed herein. The multi-chamber syringe module includes rotatably selectable fluid chambers for use with a conventional biopsy needle, such that three separate syringes are no longer needed, reducing time spent replacing syringes to improve operation speed and reduce the demands on the attention of the operating surgeon.

In one embodiment, a multi-chamber syringe module for use with a biopsy needle comprises a multi-chamber cartridge having a plurality of fluid chambers, each of the plurality of fluid chambers being selectively and temporarily deformable to create one of a fluid vacuum therein or a fluid evacuation therefrom; a luer fitting hub having a first luer fitting hub end and a second luer fitting hub end, the first luer fitting hub end configured to receive a biopsy needle; and a needle manifold having a first needle manifold end and a second needle manifold end, the first needle manifold end being fixedly coupled with the second luer fitting hub end, and the second needle manifold end being rotatably coupled to the multi-chamber cartridge to selectively fluidly couple a biopsy needle received in the first luer fitting hub end with one of the plurality of fluid chambers based on a relative rotational arrangement of the needle manifold and the multi-chamber cartridge.

In one embodiment, a method comprises providing a multi-chamber syringe module comprising a multi-chamber cartridge having a plurality of fluid chambers, each of the plurality of fluid chambers being selectively deformable to create one of a fluid vacuum therein or a fluid evacuation therefrom, a luer fitting hub having a first luer fitting hub end and a second luer fitting hub end, the first luer fitting hub end configured to receive a biopsy needle, and a needle manifold having a first needle manifold end and a second needle manifold end, the first needle manifold end being fixedly coupled with the second luer fitting hub end, and the second needle manifold end being rotatably coupled to the multi-chamber cartridge to selectively fluidicly couple a biopsy needle received in the first luer fitting hub end with one of the plurality of fluid chambers based on a relative rotational arrangement of the needle manifold and the multi-chamber cartridge; and providing a biopsy needle to be received in the first end of the luer fitting hub.

In another embodiment, a multi-chamber syringe module for use with a biopsy needle, the multi-chamber syringe module comprising: a multi-chamber cartridge having a plurality of fluid chambers, each of the plurality of fluid chambers being selectively and temporarily deformable to create one of a fluid vacuum therein or a fluid evacuation therefrom; a luer fitting hub having a first luer fitting hub end and a second luer fitting hub end, the first luer fitting hub end configured to receive a biopsy needle; and a needle manifold having a first needle manifold end, a second needle manifold end, and a manifold valve, the first needle manifold end being fixedly coupled with the second luer fitting hub end, the second needle manifold end being fixedly coupled to the multi-chamber cartridge, and the manifold valve disposed between the second needle manifold end and the multi-chamber cartridge and configured to selectively fluidly couple a biopsy needle received in the first luer fitting hub end with one of the plurality of fluid chambers based on a rotational arrangement of the manifold valve.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
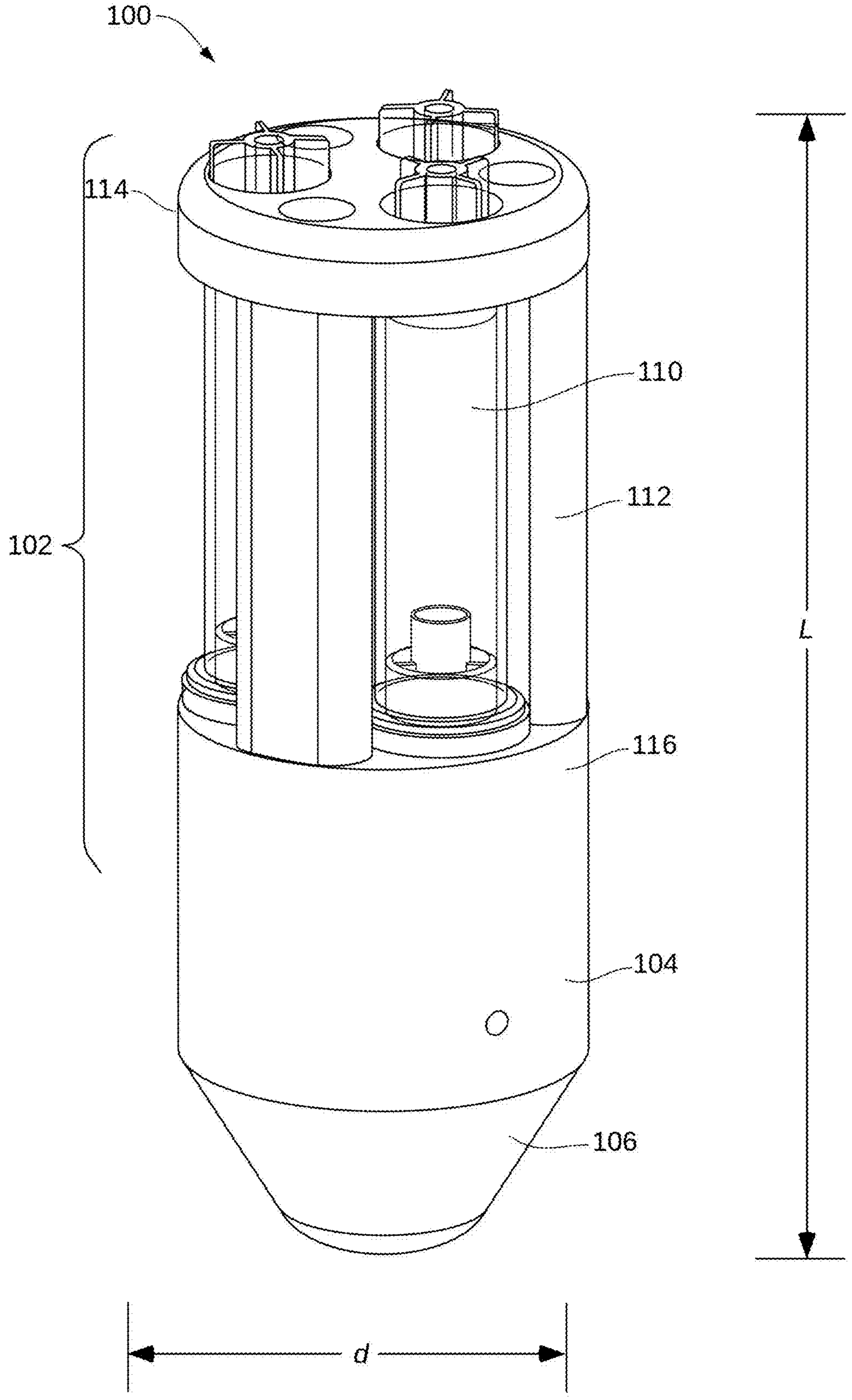
FIG. 1 is an isometric view of a multi-chamber syringe module according to embodiments described herein.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The systems and methods disclosed herein relate to a multi-chamber syringe module that couples to a conventional biopsy-type needle, which can be rigid or flexible. The multi-chamber syringe module can be used with a bronchoscope or endoscope. The multi-chamber syringe module includes a multi-chamber cartridge having a vacuum air chamber, an evacuative air chamber, and a saline chamber.

FIG. 1 is an isometric view of a multi-chamber syringe module 100 according to an embodiment. Multi-chamber syringe module 100 includes a multi-chamber cartridge 102, a needle manifold 104, and a luer fitting hub 106. In embodiments, luer fitting hub 106 is configured to couple to a standard biopsy needle via a luer fitting. In embodiments, luer fitting hub 106 can be rigid or flexible. In alternative embodiments, a screw type, snap-fit or other suitable type of connection can be used.

As shown in FIG. 1, multi-chamber cartridge 102 includes a plurality of fluid chambers 110, a chamber bracket 112, a chamber cap 114, and a chamber receptacle 116. In embodiments, chamber bracket 112 couples to chamber receptacle 116 at a bottom portion and to chamber cap 114 at a top portion. In embodiments, chamber receptacle 116 and chamber cap 114, along with chamber bracket 112, are configured to secure the plurality of fluid chambers 110 in multi-chamber cartridge 102. In the embodiment depicted in FIG. 1, multi-chamber cartridge 102 includes three fluid chambers 110. In alternative embodiments, multi-chamber cartridge 102 can include fewer or more than three fluid chambers 110, depending upon the desired functions for the fluids stored therein.

In some embodiments, fluid chambers 110 can be disposable while other components of multi-chamber syringe module 100 are reusable (e.g., can be sterilized and used in multiple procedures). In other embodiments, fluid chambers 110 are also reusable. In yet another embodiment, the entirety of multi-chamber syringe module 100 is either reusable or disposable. In general, the devices described herein are reusable in that they can be reset and used for multiple passes, and in some embodiments the entire module 100 can be disposable between patients. Accordingly, materials that are appropriate for use to make up module 100 can be similar to those used in conventional syringes and other disposable components used in medical procedures, included molded polymers, rubber or synthetic rubbers, or other relatively inexpensive, sterilizable materials.

The size and fluid capacity of fluid chambers 110 can vary in embodiments. In one example embodiment, each fluid chamber 110 can contain up to about 40 milliliters (mL) of fluid. In other embodiments, fluid chambers 110 can contain a greater or lesser volume of fluid. In still other embodiments, the fluid capacity among the plurality of fluid chambers can vary, e.g., a first fluid chamber 110 has a fluid capacity of about 60 mL and second and third fluid chambers 110 each have a fluid capacity of about 40 mL. Though not shown in FIG. 1, fluid chambers 110 can include fluid level markers or indicators on a surface thereof. In one embodiment, a chamber 110 associated with maintaining a quantity of water can have a volume sufficient to hold about 20 cc to about 50 cc of liquid, while a chamber 110 associated with maintaining a vacuum can have a volume sufficient to hold between about 10 cc and about 30 cc, while a chamber 110 associated with maintaining a volume of air can have a volume sufficient to hold about 10 cc of air.

Referring to multi-chamber syringe module 100 overall, in embodiments multi-chamber syringe module 100 can have an overall length L of about 4 inches to about 8 inches and a maximum diameter d (i.e., a diameter at its widest or largest point) of about 0.75 inches to about 2 inches. In one particular example, a length L of multi-chamber syringe module 100 is less than about 6 inches and a maximum diameter d is about 1 inch. In alternative embodiments, multi-chamber syringe module 100 can have dimensions that are larger or smaller than those given by example here.

The dimensions described above relate to particular embodiments that are designed for improved operability with FNA needles used in pulmonary treatments. In a typical procedure, a surgeon will operate an FNA needle and pass it through an area of interest, such as a tumor, multiple times. During this procedure, in a conventional approach, a syringe is attached to the top of the FNA needle, and the plunger is withdrawn such that a vacuum is present. Operation of an FNA needle is highly skilled and requires using dexterity and hand-feel to detect when the level of friction between the needle and the surrounding tissue varies. Syringe module 100 is, in one embodiment, placed in the same position where a vacuum syringe would otherwise have been located. Thus the weight and size of the syringe module 100 should not be significantly different from that of a typical luer-lock, vacuum syringe used in existing conventional procedures. In this way, additional training for the surgeon is not required, and the hand feel associated with changes in friction surrounding the needle does not vary significantly. This is because in the event that the syringe module is too heavy, the operator (e.g., surgeon) can lose dexterity due to the need to hold the combination of the FNA needle and module 100.

Thus in embodiments, the volume of each of the chambers 110 is matched to the expected size of the needle that it is to be used with. The lower bound of the volume within each chamber 110 is set by the needle or other expected use. The upper bound of the volume within each chamber 110 is set by the associated size and weight of the syringe module 100 required to contain those volumes.

For ease of explanation, as described above, one procedure in which the embodiment shown in FIG. 1 may be used is a pulmonary FNA setting to biopsy a tumor. In such embodiments, the typical volume of the needle that is used is about 2 cubic centimeters. As described below in more detail, the size of the chambers should be sized to provide sufficient vacuum to draw a desired sample into the needle, expel the sample with saline, and clear the needle with air. However, while it is helpful to have sufficient volume of vacuum, saline solution, and air to conduct the functions of sample gathering, sample depositing, and line cleaning, it should be appreciated that too much volume will increase the size and weight of the equipment to such an extent that a surgeon may not wish to use the device, or may find his or her dexterity reduced by the bulk of the syringe module 100.

Figure 2:
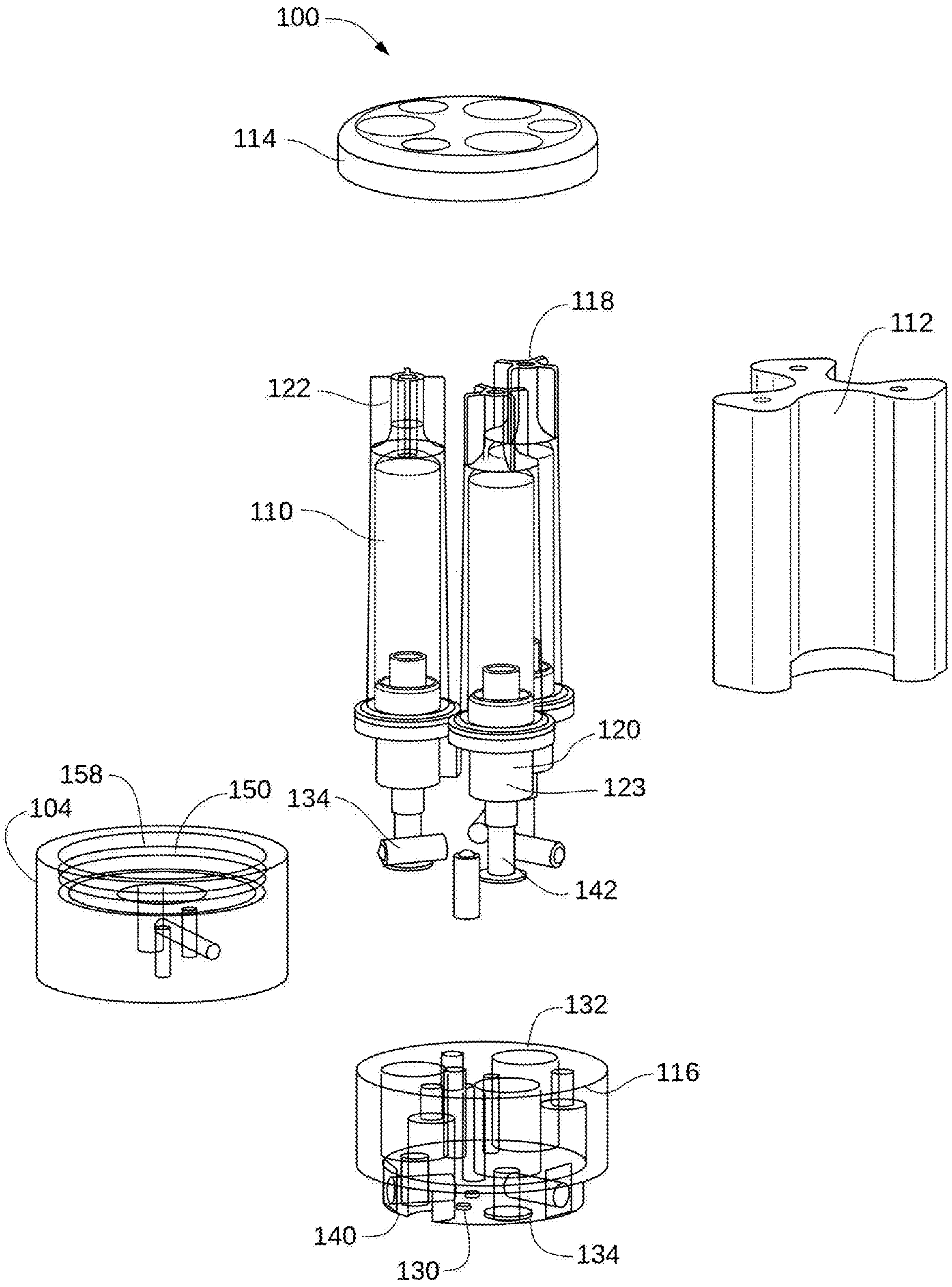
FIG. 2 is an exploded view of a multi-chamber syringe module according to embodiments described herein.

FIG. 2 is an exploded view of multi-chamber syringe module 100 previously described in FIG. 1. In the embodiment shown in FIG. 2, each fluid chamber 110 includes a filling port 118 at a first end and a chamber fitting 120 at a second end. In embodiments, each fluid chamber 110 can be filled at filling port 118 with a syringe or other device or method. Each filling port 118 can also include a one-way valve 122, which can be incorporated in an end portion of each fluid chamber 110 or separately coupled thereto (refer, for example, to valves 222 depicted in FIG. 4A). Either configuration is possible in various embodiments even if not explicitly depicted as such herein. Each one-way valve 122 can be configured to allow fluid to enter a respective fluid chamber 110 only, or conversely, exit a respective fluid chamber only. Each chamber fitting 120 can include a one-way valve 123, the one-way valve 123 configured to allow fluid to enter the chamber only, or conversely, exit the chamber only. In alternative embodiments, such as the one depicted in FIG. 4A and discussed in more detail below, a stopcock valve can either accompany one-way valve 122 or replace one-way valve 122.

In some embodiments, a pre-loaded kit can be provided so that a surgeon need not fill or evacuate each of the fluid chambers 110. For example, a kit may include a syringe module 100 and an FNA needle (not shown in this Figure), and the syringe module 100 may be preloaded with sufficient saline, air, and vacuum in appropriate chambers 110 such that a surgeon can use the kit without bothering with the valves. In such embodiments, depending upon the processes used to prepare the syringe module 100, filling ports 118 may not be included. In other kits, a syringe module 100 may be pre-loaded and may be provided separate from the FNA needle. Such kits are particularly useful when an FNA needle is reused but the corresponding syringe module 100 is disposable. In still further embodiments, the syringe module 100 can be modified such that it is usable in other procedures, including those that are not associated with FNA or pulminology whatsoever, such as in gastrointestinal procedures. Depending upon the type of procedure to be performed, the kit could include other components as necessary or appropriate.

In embodiments, part or all of each fluid chamber 110 can comprise a flexible or elastic material, such as a plastic, silicone rubber, or another suitable elastic material. In such embodiments, the elasticity and flexibility of each fluid chamber 110 allows each fluid chamber 110 to function as a pump (i.e., to pull fluid in or push fluid out) when a user selectively and alternately compresses and relax the wall of a selected fluid chamber 110. This selective and temporary deformation, which can be done by hand if the side of the fluid chamber 110 is accessible on the side of the syringe module 100 as shown in FIG. 1, can cause a fluid chamber 110 to temporarily and selectively apply a vacuum (e.g., inward) fluid flow or cause an evacuative (e.g., outward) fluid flow at one or both of filling port 118 and chamber fitting 120. In some embodiments, ergonomic detents or other haptic markers can be arranged on an exterior portion of each fluid chamber 110 to assist the user in gripping fluid chamber 110 or to distinguish between different ones of the plurality of fluid chambers 110 during pumping or evacuation. For example, a first pattern of haptic markers can identify a fluid chamber 110 configured to apply a vacuum force, and a second pattern of haptic markers can identify a fluid chamber 110 configured to apply an evacuative force. In alternative embodiments, the material composition of fluid chamber 110 can be rigid, with pumping and vacuum operations facilitated by a pumping mechanism incorporated into or coupled with one or more fluid chambers 110, or by an external syringe or mechanical pump/vacuum device.

In embodiments, one or more of the plurality of fluid chambers 110 can be configured as a vacuum fluid chamber. In a vacuum embodiment of a fluid chamber 110, filling port

118 can include an exit-only one way valve 122 and chamber fitting 120 can include an enter-only one way valve 122. Once fluid chamber 110 is squeezed, the combination of one-way valves 122 and the resiliency force created by depressing the walls of fluid chamber 110 together creates a vacuum within fluid chamber 110. In embodiments, the vacuum embodiment of a fluid chamber 110 can be capable of creating −20 mm $H_2O$ to −350 mm $H_2O$ of vacuum. The fluid vacuum created in this embodiment is transferred through chamber fitting 120, needle manifold 104, luer fitting hub 106, and eventually to a biopsy needle.

In embodiments, fluid chamber 110 can be configured as an evacuative fluid chamber 110. In this embodiment of fluid chamber 110, the user squeezes the walls of fluid chamber 110 to pump the contents—air, saline or some other fluid—through chamber fitting 120, needle manifold 104, luer fitting hub 106, and a biopsy needle. In an evacuative embodiment of a fluid chamber 110, filling port 118 can include an enter-only one way valve 122 and chamber fitting 120 can include an exit-only one way valve 122.

In embodiments, multi-chamber syringe module 100 can include one vacuum-type fluid chamber 110 and two evacuative fluid chambers 110. In this embodiment, one of evacuative fluid chambers 110 can be configured to contain air, and one of the evacuative fluid chambers 110 can be configured to contain a saline solution or other suitable flushing or medicament solution.

In an alternative embodiment not depicted, multi-chamber syringe module 100 includes two rather than three fluid chambers 110. In this embodiment, a single pump/vacuum type fluid chamber 110 can replace the evacuative fluid chamber 110 which contains air and the vacuum-type fluid chamber. The pump/vacuum type fluid chamber 110 can include a selective two-way valve arranged within filling port 118 and chamber fitting 120 to accomplish both positive and negative pressure functions. In still other embodiments, multi-chamber syringe module 100 can include more than three or fewer than two fluid chambers 110.

Figure 3A:
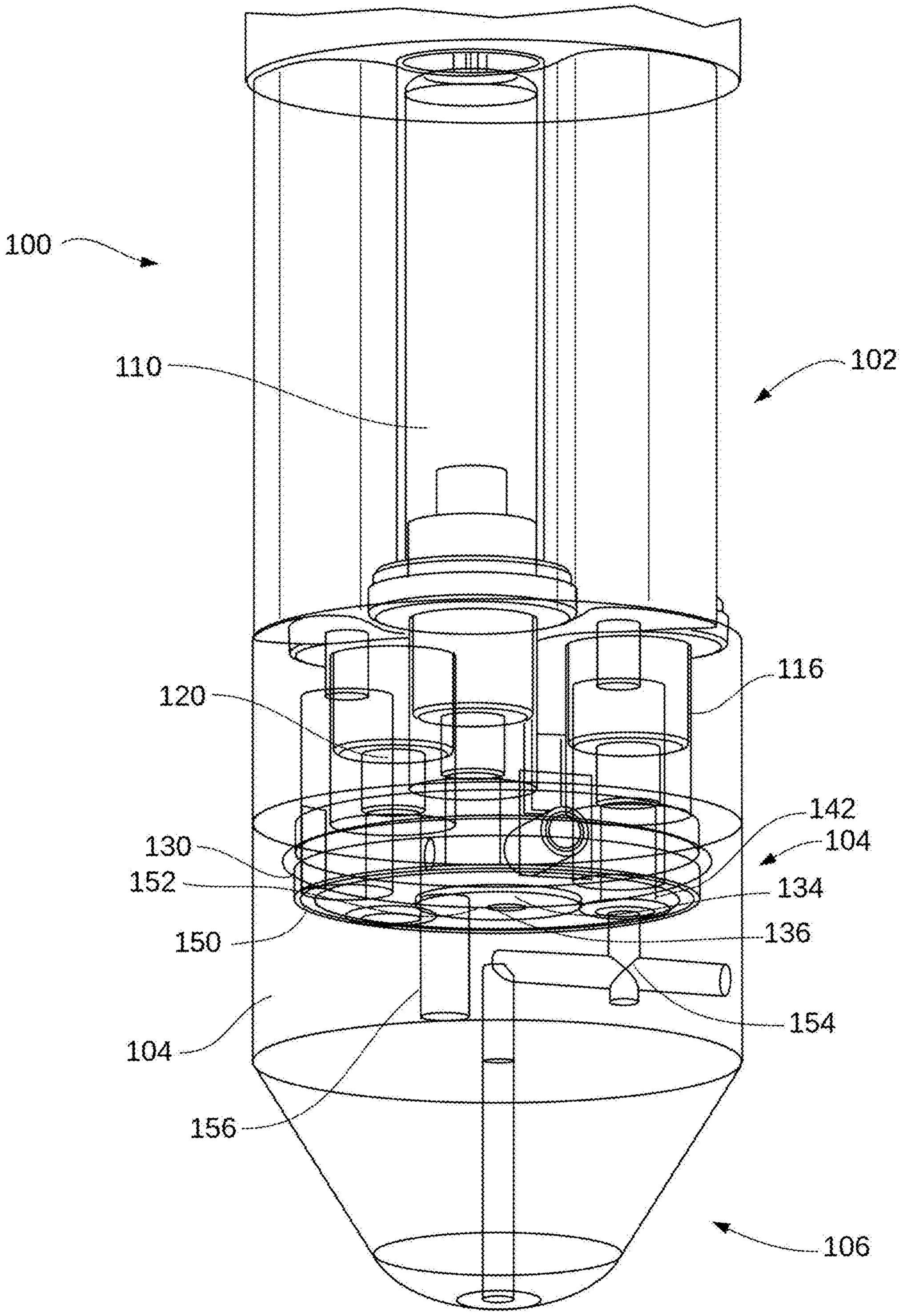
FIGS. 3A and 3B are transparent, isometric views of a multi-chamber syringe module according to embodiments described herein.
Figure 3B:
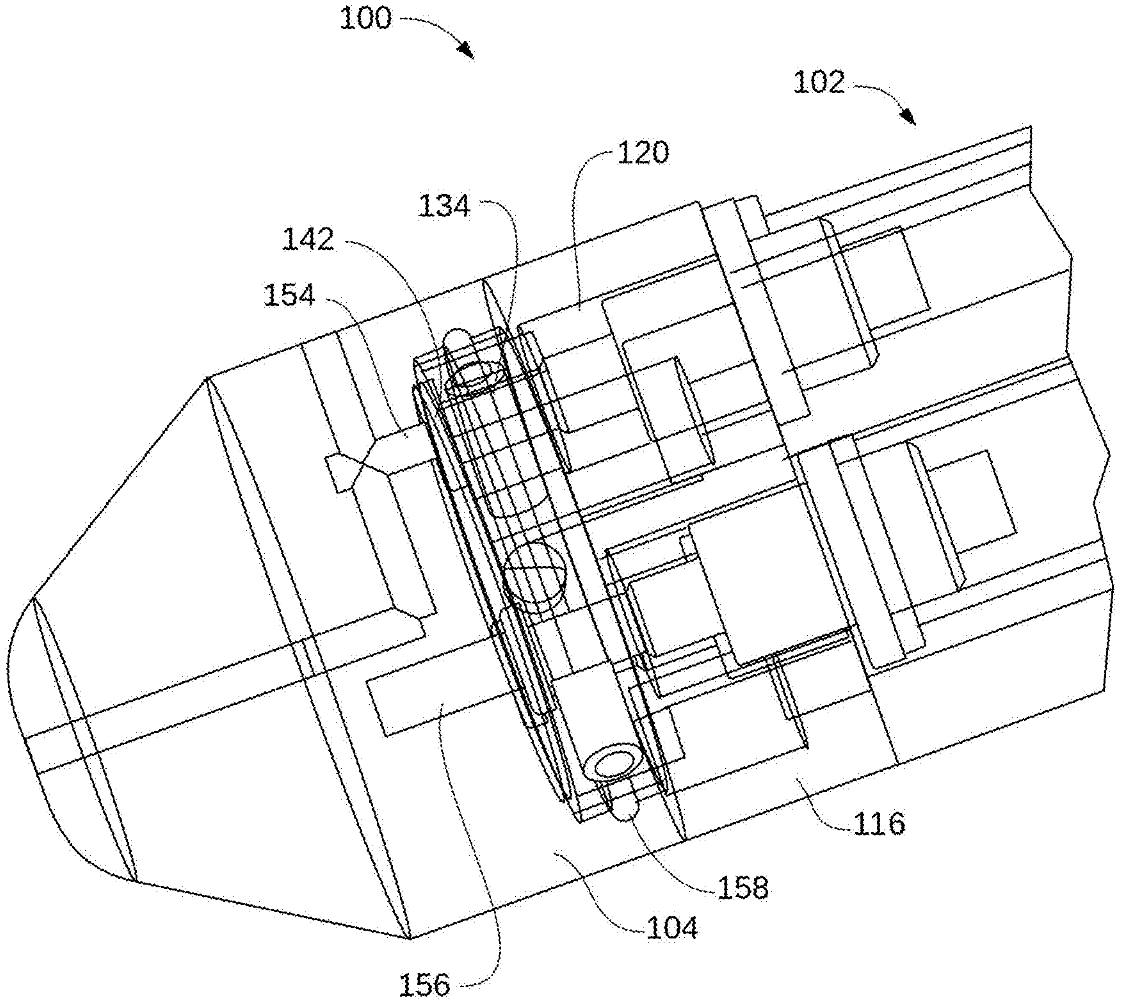

Referring also to FIGS. 3A and 3B, chamber receptacle 116 can include a receptacle rotation surface 130, a plurality of fluid ports 132, a first rotation coupling 134, and a plurality of centering ball-nose spring plungers 134. Receptacle rotation surface 130 can be arranged on a first end or bottom portion of chamber receptacle 116 and further includes a circular array of detents 136, as shown in that embodiment. A circular array of detents 136 can be concentric with a central axis of multi-chamber syringe module 100. Each fluid port 132 thus extends from a second end or top portion of chamber receptacle 116 to rotation surface 130. Further, fluid ports 132 are configured to align with fluid chambers 110 and are thus offset from the central axis of multi-chamber syringe module 100 by an offset distance. As shown in FIGS. 3A and 3B, first rotation coupling 134 can also be arranged on rotation surface 130. Centering ball-nose spring plungers 134 are thus radially arranged within chamber receptacle 116 and are further outwardly facing and adjacent to rotation surface 130.

Returning to FIG. 2, each fluid port 132 (in embodiments, a number of fluid ports 132 and other elements discussed herein will correspond with a number of fluid chambers 110) further includes an aperture 140 and an o-ring 142 arranged on rotation surface 130. Each fluid port 132 shown in FIG. 2 is therefore configured to selectively receive and secure a chamber fitting 120 of a respective fluid chamber 110. As described above with respect to FIG. 1, in alternative embodiments kits or devices can be provided that are pre-loaded or unitary, such that there is no need for such mating engagement between the fluid ports 132 and any component of the syringes 110. In the embodiment shown in FIG. 2, however, chamber fitting 120 is received at the top portion of fluid port 132 and rests at the bottom portion of fluid port 132 such that chamber fitting 120 couples to aperture 140 and an o-ring 142. Each fluid port 132 therefore couples to one fluid chamber 110. In other words, an embodiment of multi-chamber syringe module 100 having three fluid chambers 110 will have a chamber receptacle 116 that includes three fluid ports 132.

Needle manifold 104 of FIG. 2 includes a manifold rotation surface 150, a second rotation coupling 152, a manifold fluid port 154, and one or more indicating ball-nose spring plungers 156 (FIG. 3A). A bottom portion or first end of needle manifold 104 interfaces or couples with luer fitting hub 106 (see, e.g., FIG. 3A), and manifold rotation surface 150 is arranged on a top portion or second end of needle manifold 104. Manifold rotation surface 150 further includes an inner groove 158 arranged on an inward facing wall of manifold rotation surface 150, and second rotation coupling 152 is centrally arranged on manifold rotation surface 150. Manifold fluid port 154 is also arranged on manifold rotation surface 150. Manifold fluid port 154 may not be centrally located on manifold rotation surface 150, and can be configured to selectively align with aperture 140 and adjacent o-ring 142 of one of the plurality of fluid ports 132 and is thus located at the same offset distance away from the central axis of rotation of multi-chamber syringe module 100. In embodiments, indicating ball-nose spring plunger 156 can be arranged parallel to, but offset from, the axis of rotation of multi-chamber syringe module 100.

First rotation coupling 134 of chamber receptacle 116 is configured to rotatably couple to second rotation coupling 152 of needle manifold 104 in the embodiment shown in FIG. 3A. The rotatable coupling of first rotation coupling 134 and second rotation coupling 152 enables multi-chamber cartridge 102 and needle manifold 104 to rotate with respect to each other. In various embodiments, first rotation coupling 134 and second rotation coupling 152 can comprise a male-and-female bearing coupling or some other suitable rotatable coupling. In order to enforce a particular order of events (such as sample collection, provision of saline, and then provision of air) it may be desirable to include a ratchet and pawl or other one-way rotation mechanism to prevent accidental misuse of the device.

To reduce the amount of free play arising from the rotatable coupling of first rotation coupling 134 and second rotation coupling 152, centering ball-nose spring plunger 134 of chamber receptacle 116 can be arranged to provide a plunger force in a direction orthogonal to the axis of rotation of multi-chamber cartridge 102. In one embodiment, and as seen in FIGS. 3A and 3B, three or more centering ball-nose spring plungers 134 are coupled to chamber receptacle 116 and configured to forcibly engage with inner groove 158 of manifold rotation surface 150. Centering ball-nose spring plungers 134 that are engaged with inner groove 158 can provide the benefits of automatic centering and increased stability during rotation of chamber receptacle 116 with respect to needle manifold 104.

In embodiments, offset manifold fluid port 154, which selectively aligns with one of the plurality of fluid chambers 110, allows a user to select which fluid chamber 110 he or she wishes to be in fluid engagement with a biopsy needle coupled to multi-chamber syringe module 100. This is because apertures 140 and adjacent o-rings 142, each of which corresponds to one of the plurality of fluid chambers 110, are configured to sealably engage with manifold rotation surface 150. At the same time, apertures 140 and adjacent o-rings 142 are configured to selectively and fluidly engage with manifold fluid port 154. In other words, one aperture 140 and adjacent o-ring 142, if selectively aligned with manifold fluid port 154, will be sealably engaged with manifold rotation surface 150 but allow fluid engagement with manifold fluid port 154. The particular fluid chamber 110 that is aligned with manifold fluid port 154 will be in fluid engagement with a biopsy needle coupled multi-chamber syringe module 100 at luer fitting hub 106. The remaining apertures 140 and adjacent o-rings 142 that are not aligned with manifold fluid port 154 will be sealably engaged with manifold rotation surface 150 and allow no fluid engagement with the non-aligned fluid chambers 110 and the biopsy needle (nor, for that matter, leakage of the contents within or loss of vacuum).

To aid the user in selecting and assuring alignment of one of the plurality of fluid chambers 110 with manifold fluid port 154, indicating ball-nose spring plunger 156 of needle manifold 104 is configured to engage with any one of detents 136 of chamber receptacle 116. Detents 136 and indicating ball-nose spring plunger 156 are arranged such that indicating ball-nose spring plunger 156 is engaged with one of the plurality of detents 136 when an aperture 140 and adjacent o-ring 142 aligns with the singular manifold fluid port 154. When the user feels detents 136 and indicating ball-nose spring plunger 156 engage with each other, the user is informed, by haptic feedback, that an aperture 140 and o-ring 142 is aligned with manifold fluid port 154. Further, a set of external indicators (not depicted in FIG. 3A) arranged on the surfaces of chamber receptacle 116 and manifold 104 and configured to provide a visual indication by aligning with one another can further inform the user which fluid cartridge is in fluid engagement with manifold 104. Visual indications can be used not only to indicate which of the chambers 110 is in fluid communication with the needle, but also which direction of rotation should be used to proceed to the next step in a typical surgical process, as described in more detail below.

Figure 4A:
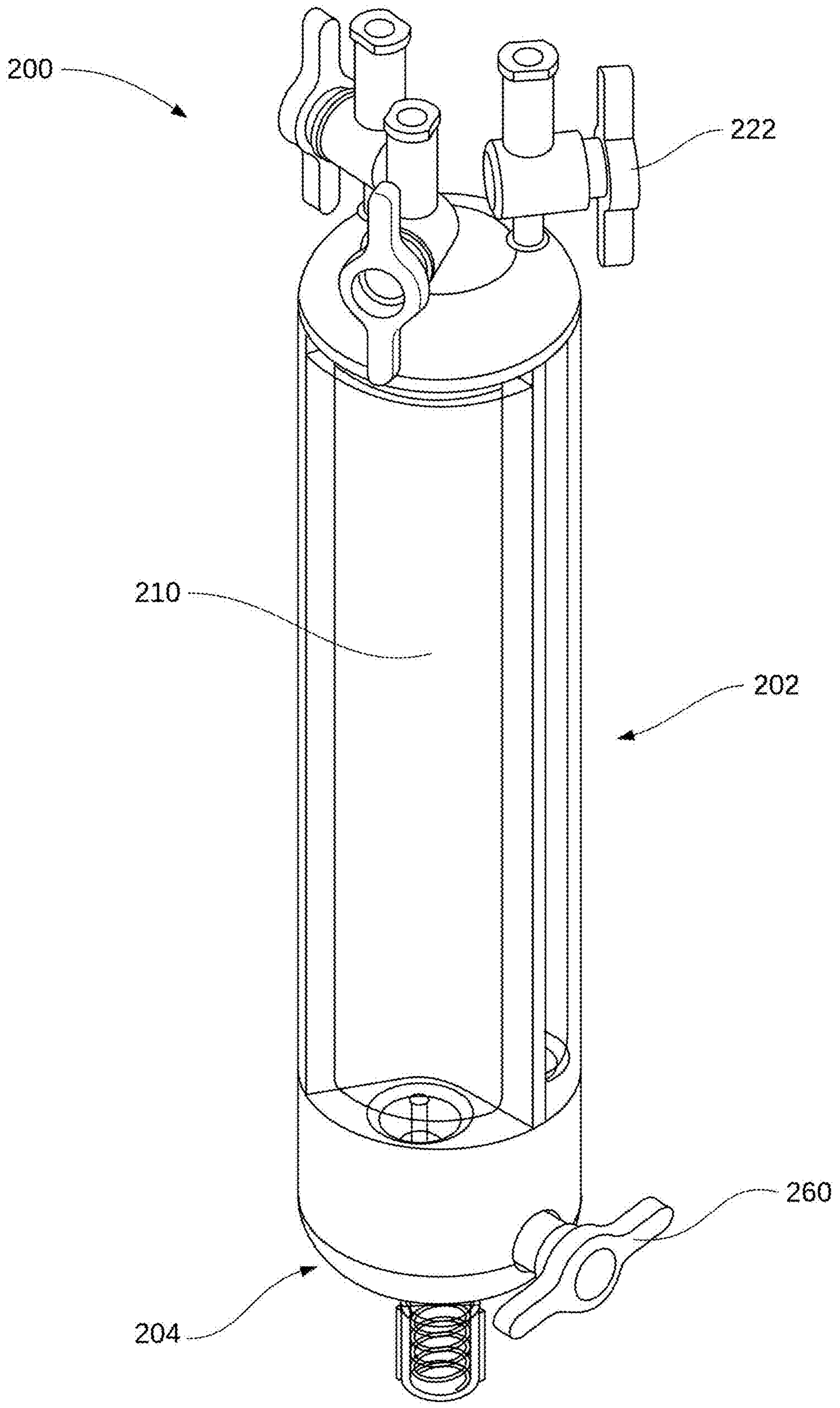
FIG. 4A is an isometric view of a multi-chamber syringe module according to embodiments described herein.
Figure 4B:
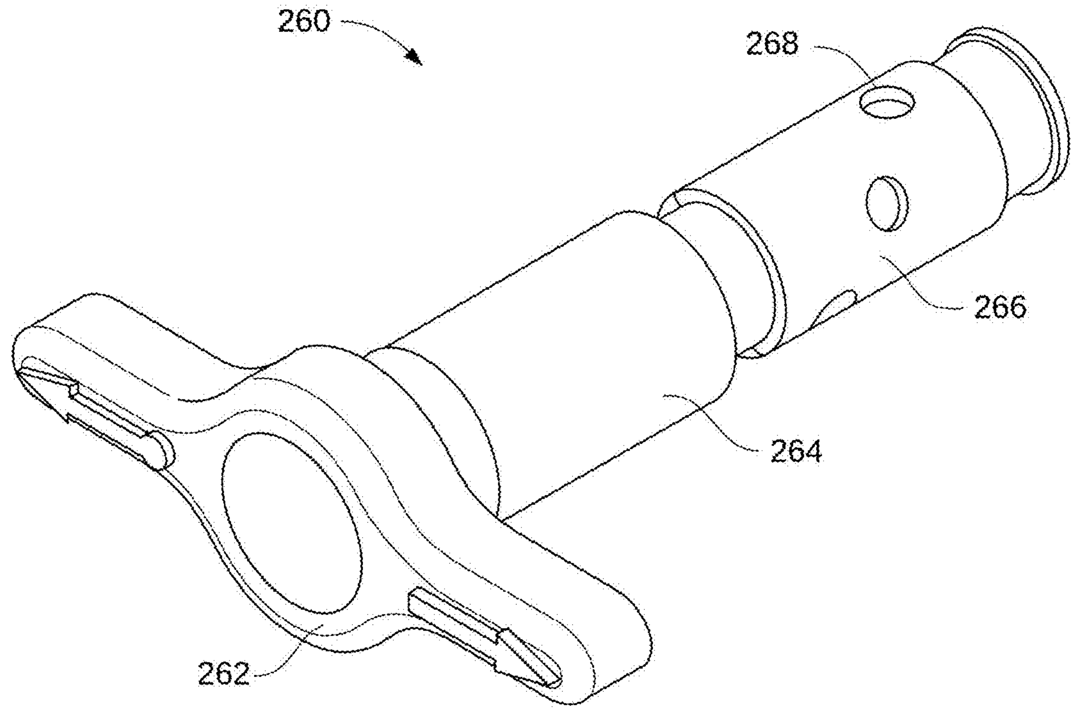
FIG. 4B is an isometric view of a multi-chamber valve of a multi-chamber syringe module according to embodiments described herein.
Figure 4C:
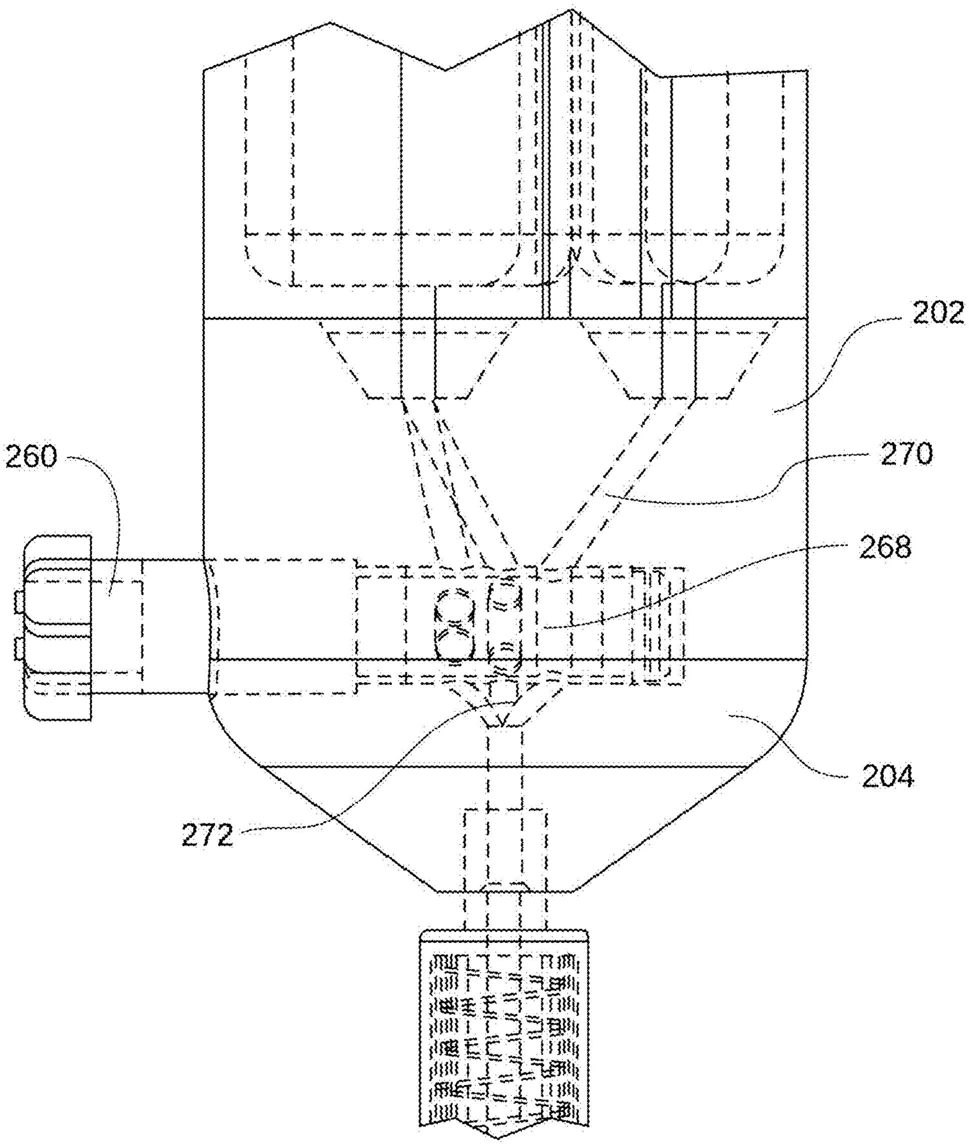
FIG. 4C is a transparent line drawing of a multi-chamber syringe module according to embodiments described herein.

FIGS. 4A-4C depict a multi-chamber syringe module 200 according to another embodiment in which external stopcocks are used to prepare the syringe module 200, rather than hand-compressible sides. Multi-chamber syringe module 200 includes a multi-chamber cartridge 202 and a needle manifold 204. In this embodiment, and in contrast with multi-chamber syringe module 100 discussed above, multi-chamber cartridge 202 and needle manifold 204 do not rotate with respect to each other. Instead, needle manifold 204 further includes a multi-chamber valve 260, which is configured to allow a user to select which one of a plurality of fluid chambers 210 is in fluidic engagement with a biopsy needle coupled to module 200.

As depicted in FIG. 4B, multi-chamber valve 260 includes a handle 262 at a first end, a shaft 264, and a selection barrel 266 at a second end. Selection barrel 266 includes a plurality of selectively spaced and oriented apertures 268. In this embodiment, apertures 268 are arranged and spaced apart from one another such that, at any orientation and as multi-chamber valve 260 interacts with other components of module 200, only one aperture 268 is capable of permitting fluid flow therethrough. For example, apertures 268 can be arranged at 60 degrees from each other around the central axis of selection barrel 266, though in other embodiments they can be spaced more closely with each or further apart from each other.

In embodiments, multi-chamber valve 260 can include a pull-to-engage or push-to-engage feature such that rotation of multi-chamber valve 260 by a user is only possible if the user pushes or pulls handle 262 before attempting rotation of selection barrel 266. In other embodiments, multi-chamber valve 260 can more freely rotate. In some embodiments, multi-chamber valve 260 can include a ball spring plunger and detents configured to provide haptic feedback to the user as barrel 266 is engaged or disengaged by rotation during use. Similar to the embodiments described above with respect to FIGS. 1 through 3B, it may be desirable to position the passageways through valve 260 so that, during a typical procedure, they will be used sequentially. For example, in one embodiment the furthest extended position of valve 260 corresponds to all chambers 210 being disconnected from an FNA needle (not shown), a second-from-outer position of the valve 260 corresponds to a vacuum chamber 210 being connected to the FNA needle, a third-from-outer position of the valve 260 corresponds to a saline chamber 210 being connected to the FNA needle, and a fourth-from-out position of the valve 260 corresponds to an air chamber 210 being connected to the FNA needle. Similar order can be provided in other embodiments that rely on, for example, rotation.

As depicted in FIG. 4C, multi-chamber valve 260 is configured to selectively allow fluid engagement with one of fluid chambers 210 depending on the rotational orientation of multi-chamber valve 260. Multi-chamber cartridge 202 includes chamber ports 270, and needle manifold 204 includes manifold ports 272. In this embodiment, each fluid chamber 210 has a respective chamber port 270, manifold port 272, and selectively aligning aperture 268. A selected one of the plurality of fluid chambers 210 is in fluidic engagement with the biopsy needle when an associated one of the pluralities of apertures 268 of selection barrel 266 is aligned with both a chamber port 270 and a manifold port 272. The configuration of multi-chamber valve 260 is such that when one fluid chamber 210 is in fluidic engagement with the biopsy needle, the other fluid chambers 210 are sealed, as their respective aperture 268 are not aligned with the respective chamber port 270 and manifold port 272. In this way, a particular fluid chamber 210 is selectable by the user by rotating handle 262 such that the related aperture 268 aligns with the related chamber port 270 and a manifold port 272.

Figure 5:
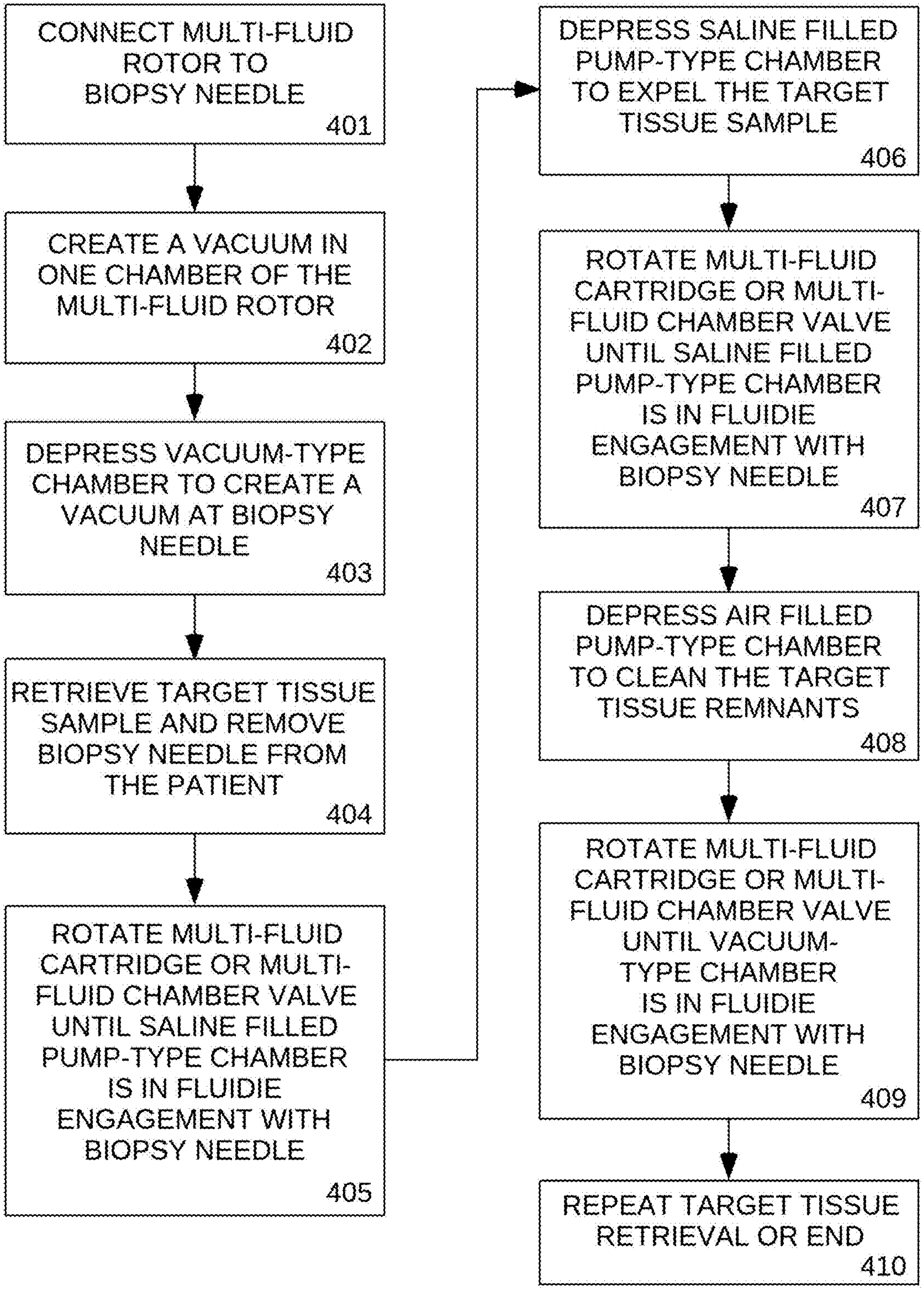
FIG. 5 is a flowchart of a method of using a multi-chamber syringe module in a fine needle aspiration procedure according to embodiments described herein.

In use, and referring also to FIG. 5, multi-chamber syringe module 100 or 200 is used in a FNA or other procedure. At 401, a user connects multi-chamber syringe module 100 or 200 to a standard biopsy needle (or some other suitable needle or device). As described above, in some embodiments connecting the multi-fluid rotor to a biopsy or other needle is not strictly requires, such as when a kit is provided in which the needle is either pre-connected, or when the needle and the mult-fluid rotor are integrally formed with one another.

At 402, optionally, the user depresses the vacuum chamber to create a vacuum via a one-way valve. Alternatively, the user can connect a vacuum source to one of the chambers within the multi-fluid rotor. Finally, in some embodiments, a vacuum may have been created in a chamber within the multi-fluid rotor. Before proceeding to 403, a vacuum is created either by manual manipulation, vacuum source, or having been provided with the rotor itself.

At 403, the user rotates multi-chamber cartridge 102 with respect to manifold 104, or rotates multi-chamber valve 260, until a vacuum-type fluid chamber 110 is in fluidic engagement with manifold 104 or 204 and therefore in fluidic engagement with the biopsy needle. The user can confirm that vacuum-type fluid chamber 110 is in fluidic engagement with manifold 104 when the user sees that vacuum-type fluid chamber 110 is in position to be in fluidic engagement with manifold 104 and feels detents 136 and indicating ball-nose spring plunger 156 engage with each other. In multi-chamber syringe module 200, ball spring plunger and detents of multi-chamber valve 260 of can provide similar haptic feedback.

At 404, the user retrieves the target tissue sample via standard biopsy removal techniques. The biopsy needle containing the target tissue sample is then removed from the patient. The vacuum provided at 403 assists with the removal of the tissue to be sampled. That is, at 404, as the user passes the needle through the tissue to be biopsied, the vacuum source is used to draw sample from a patient.

At 405, the user rotates multi-chamber cartridge 102 with respect to manifold 104, or rotates multi-chamber valve 260, until a saline-filled fluid chamber 110 or 210 is in fluidic engagement with manifold 104 or 204 and therefore in fluidic engagement with the biopsy needle. At 406, the user removes the biopsy or FNA needle from the patient, places the end of the needle in a container for sample collection, and presses and releases the saline-filled evacuative chamber 110 or 210 until the target tissue sample is expelled from the biopsy needle, such as onto a slide, into a vial, or to be captured in some other way.

At 407, the user rotates multi-chamber cartridge 102 with respect to manifold 104, or rotates multi-chamber valve 260, until an air filled evacuative fluid chamber 110 or 210 is in fluidic engagement with manifold 104 or 204, and therefore in fluidic engagement with the biopsy needle. At 408, the user presses and releases air-filled evacuative chamber 110 or 210 to clean the target tissue remnants from the biopsy needle. At 409, the user rotates multi-chamber cartridge 102 with respect to manifold 104, or rotates multi-chamber valve 260, until the vacuum-type fluid chamber 110 or 210 is again in fluidic engagement with manifold 104 or 204, and therefore in fluidic engagement with the biopsy needle.

At 410, the user can repeat the FNA, such as at another site on the patient, or end the procedure. It will be understood that the vacuum, water, and saline sources can be replenished between passes Embodiments of the multi-chamber syringe module discussed herein can be provided as a kit, as described above. For example, a kit can comprise a multi-chamber syringe module and one or more biopsy or other needles or devices configured for use with the multi-chamber syringe module. The kit further can comprise instructions for use, which can include text and diagrams of how to do one or more of: couple a needle with multi-chamber syringe module, rotate and select a desired one of a plurality of fluid chambers of the multi-chamber syringe module, remove a tissue sample obtained using the multi-chamber syringe module, remove the needle from the multi-chamber syringe module, remove or replace components of the multi-chamber syringe module (e.g., disposable or reusable fluid chambers), and sterilize components or the entirety of the multi-chamber syringe module after use. Optionally, a kit can comprise one or more disposable or replaceable components of the multi-chamber syringe module; for example, in one embodiment the fluid chambers are single-use.

Embodiments of multi-chamber syringe module 100 and 200 and related systems and method provide numerous improvements over conventional devices, systems and methods. Because multi-chamber syringe module 100 and 200 includes a fluid chamber that pumps air, a fluid chamber that creates a vacuum, and a fluid chamber that pumps saline, and because these chambers are conveniently configured to be operated as hand pumps, there is no longer the need for three separate syringes and three separate attachment and reattachment tasks for every pass as in conventional approaches. A user can simply grip the needle manifold and rotate the multi-chamber cartridge to align a different fluid chamber when a different fluid is required. Or, in multi-chamber syringe module 200, the user can rotate the multi-chamber valve to select a different fluid chamber when a different fluid is required. In this way, multi-chamber syringe modules 100 and 200 can save time, improve convenience, and reduce cost (both related to material/device costs and operating room and physician time) associated with each biopsy search procedure.

Figure 6:
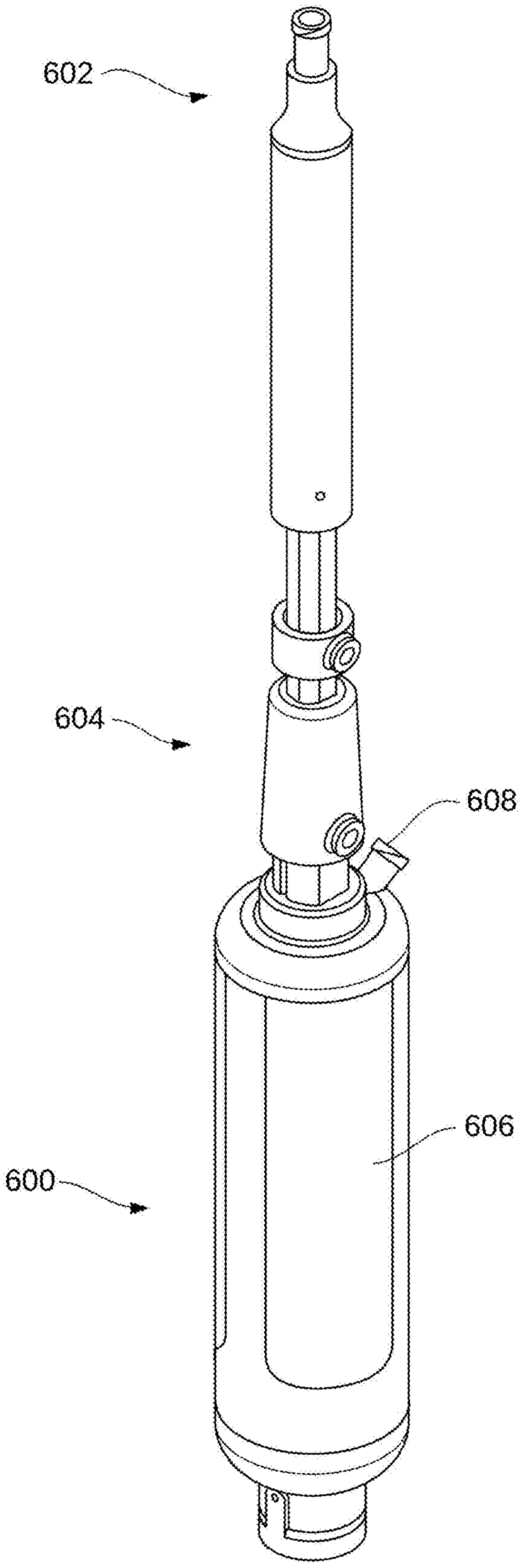
FIG. 6 is a perspective view of a multi-fluid rotor system including an FNA controller, according to an embodiment.

FIG. 6 depicts an assembled embodiment of a multi-fluid system 600 coupled to an FNA needle 602. As shown in FIG. 6, a coupling mechanism 604 connects multi-fluid system 600 with FNA needle 602. Multi-fluid system 600, as described in more detail below with respect to FIGS. 7-17, is designed to increase available air, saline, and vacuum volume while limiting additional mass attached to the end of the FNA needle 602.

Before proceeding, it should be understood that the embodiment shown in FIGS. 6-17 relate to the specific, individual embodiment in which an FNA needle (which typically includes a luer-lock connector for coupling to a syringe) is directly connected to a multi-fluid system (600). In alternative embodiments, as described in more detail below with respect to FIGS. 18A-18C, the needle (which may be an FNA needle or some other type of needle used in another procedure) can be arranged either at the distal or the proximal end of the multi-fluid system, and the disclosure herein related to the embodiment of FIGS. 6-17 can be modified as appropriate.

Returning to FIG. 6, multi-fluid system 600 includes side panel 606, which is made of a conformable material that can be compressed or released by a user. Although only one side panel 606 is visible in the view of FIG. 6, there are typically three side panels 606 (i.e., one associated with the provision of a vacuum, one with saline, and one with air).

The embodiment shown in FIG. 6 also includes side port 608. Side port 608 can be used to add water to the multi-fluid system 600 for replenishment before or during use. This port could be arranged elsewhere, such as at the proximal end of the multi-fluid system 600, in alternative embodiments. Additional ports can be present in embodiments, such as incorporation of an additional passage towards FNA needle 602 so that a guidewire or other cleaning wire can pass to the obstruction while the vacuum, air, and saline chambers are not connected.

Figure 6A:
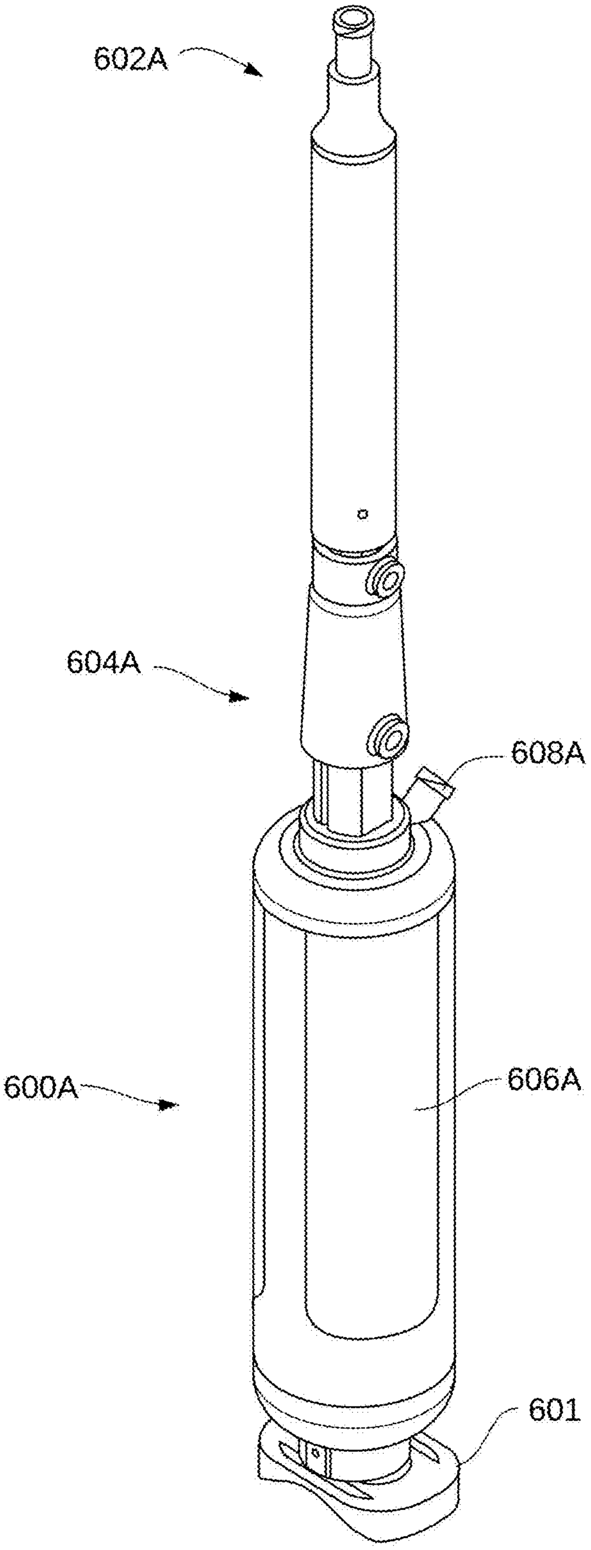
FIG. 6A is a perspective view of an alternative embodiment of a multi-fluid rotor system including an FNA controller, incorporating a plunger.

FIG. 6A is an alternative embodiment in which the components 600A, 602A, 604A, 606A, and 608A are substantially similar to their counterparts (600, 602, 604, 606, and 608, respectively) as described above with respect to FIG. 6. Additionally, the embodiment shown in FIG. 6A includes a plunger 601. Plunger 601 can be used in embodiments where the side panels 606A are not manually deformable. In some cases, a plunger can be incorporated even where the side panels 606A are manually deformable, such that an operator has a choice of which mode of operation to use, either squeezing the side panel 606A or using the plunger 601 to push fluid into or out of the various chambers within the multi-fluid system 600A. However, there are some advantages to a hard-sided side-panel 606A, since a plunger 601 may provide for more complete expulsion of the fluid within a chamber, for example, than would otherwise be possible if squeezing a deformable side panel 606.

As shown in FIG. 6A, plunger 601 is elongated in one direction. The engagement between the plunger and the particular chamber to be used in a procedure can be set in some embodiments by rotating the plunger 601, similar to the rotation of chamber cap 614 described below with respect to the embodiment of FIG. 6. In both embodiments (i.e., 600 of FIG. 6 as well as 600A of FIG. 6A) the fluid chambers are temporarily deformable. The term "temporarily deformable," as used herein, refers to the ability to manipulate the fluid volume of the chamber, either by compressing that chamber by hand (via the deformable side-panels 606A, 606B, and 606C of FIG. 6) or, alternatively, by compressing the volume via a plunger (e.g., plunger 601 of FIG. 6A).

Figure 7:
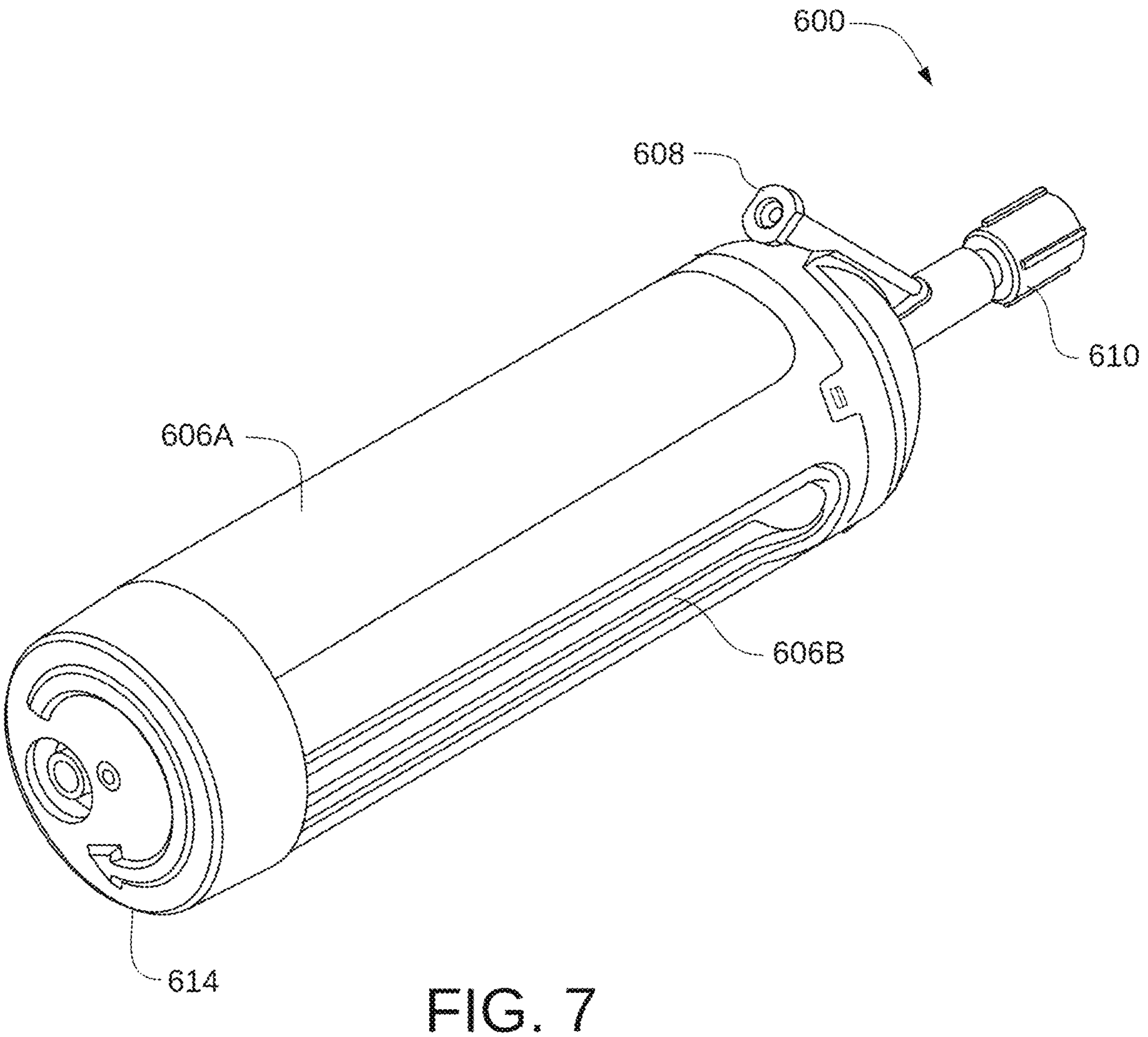
FIG. 7 is a perspective view of the multi-fluid rotor of FIG. 6.

FIG. 7 is a perspective view of multi-fluid system 600, in a packaged state. As shown in FIG. 7, system 600 includes side panels 606A and 606B, which are configured to house different fluids (or vacuum) as described above. Furthermore, cap 610 is arranged over the luer lock connection to an adjacent component (such as an FNA needle or other similar device).

FIG. 7 further shows chamber cap 614, which is similar to chamber cap 114 previously described with respect to FIG. 2. Chamber cap 614, in the embodiment shown in FIG. 7, includes an indication of which chamber is coupled to the outlet of the device (i.e., behind cap 610), as well as indications of which direction the cap should be rotated during normal use. As chamber cap 614 is rotated, different ones of the chambers (e.g., the cavities behind side panels 606A and 606B) are fluidically coupled to the passage behind cap 610.

Figure 7A:
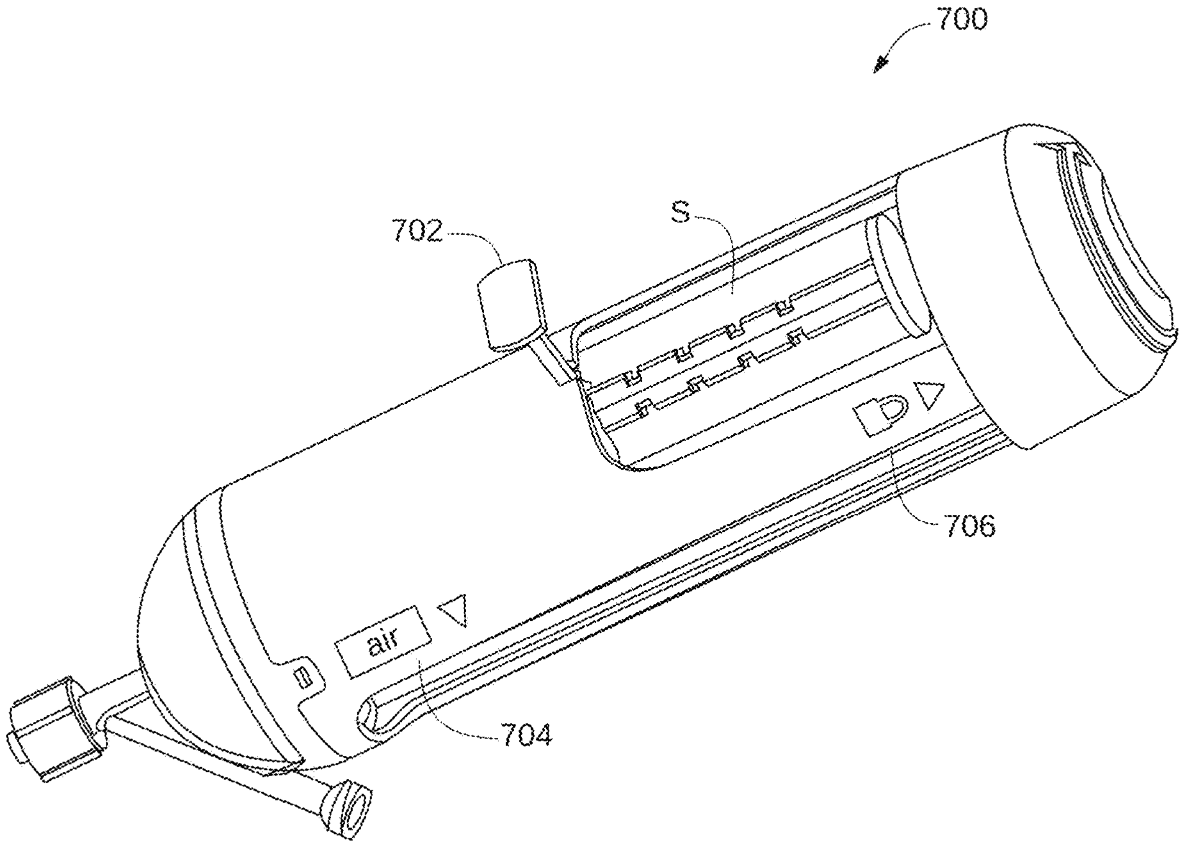
FIG. 7A is a perspective view of an alternative embodiment of a multi-fluid rotor having a plunger.

FIG. 7A is an alternative embodiment of a multi-fluid system 700 that incorporates a plunger control 702. Plunger control 702 can be more easily manipulated, and can be more accurately controlled to dispense or withdraw a predefined quantity of fluid, in embodiments. The embodiment shown in FIG. 7A includes only one plunged container, associated with plunger control 702, and the exposed portion of the shaft S includes notches that are configured to cause each depression of the control 702 to dispense the desired quantity of a fluid in the associated chamber (not shown). In alternative embodiments any number of the containers may be plunged.

FIG. 7A also shows fluid indicator 704 and lock indicator 706, which can be incorporated into any of the embodiments described herein. Fluid indicator 704 indicates the fluid housed within the associated chamber. In embodiments, this indicator can be engraved into the system 700 itself, or alternatively the indication could be provided by use of a color scheme (e.g., red for vacuum, white for air, and blue for saline or water) that will assist a user in confirming that the correct chamber has been selected before use. In embodiments, the indicator could be an LED or other light source that lights up a color corresponding to the currently-engaged chamber (e.g., again, red, blue, or white). Similarly, lock indicator 706 can be used to indicate a lock position such that the chamber will not be inadvertently switched or misaligned during use. Other lock indicators 706 could include, for example, notches, toggle switches or mechanical locks, or LEDs or other lights that only emit a light when the device is in a locked state.

Figure 8:
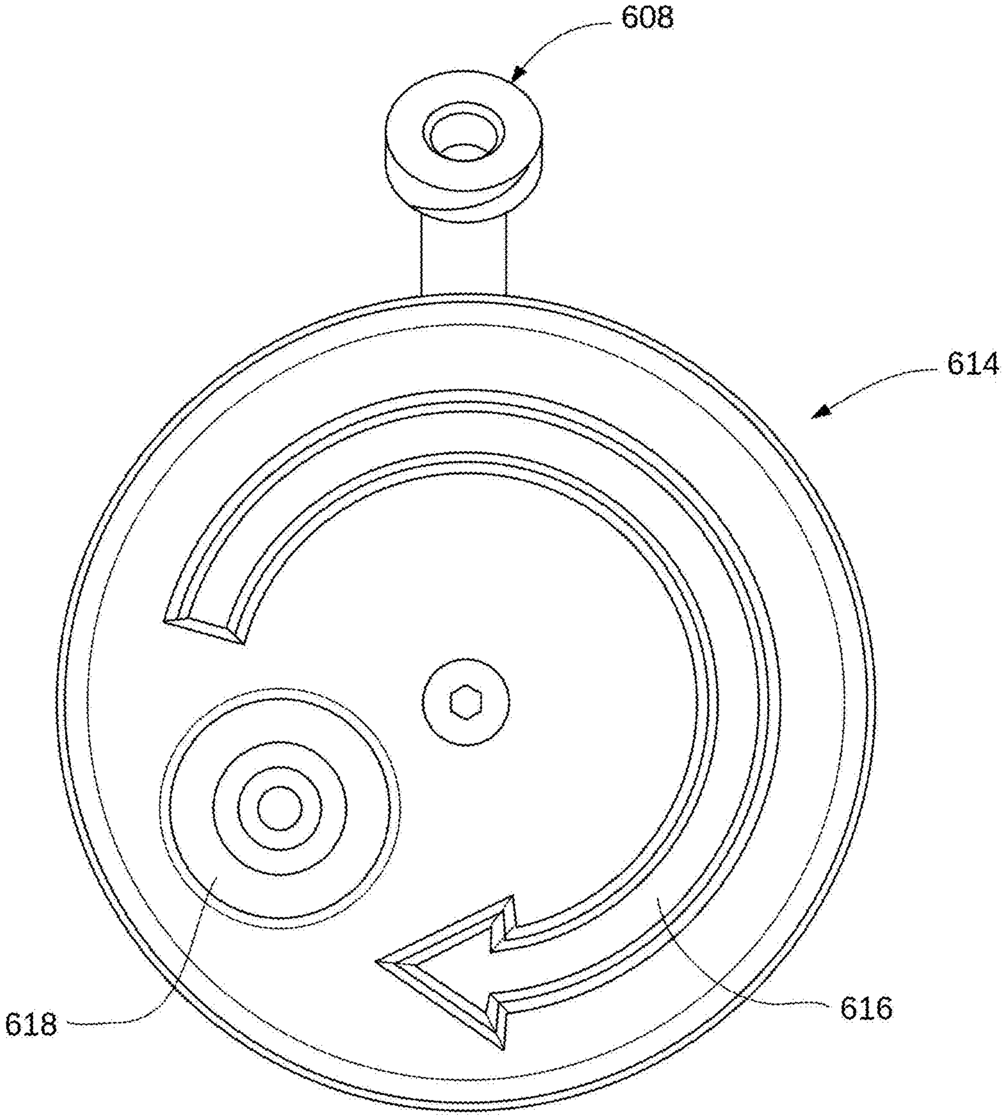
FIG. 8 is a top view of the multi-fluid rotor of FIG. 6.

FIG. 8 is a top view of the multi-fluid system 600 of FIGS. 6 and 7. Based on the available perspective in this top view, only the chamber cap 614 and the side port 608 are visible. In the embodiment shown in FIG. 8, the top view includes both an arrow 616 indicating a direction of rotation during normal use, as well as an indicator 618 that illustrates the currently engaged chamber (i.e., which of the chambers is fluidically coupled to the outlet behind cap 610.

In the embodiment shown in FIG. 8, there can be four positions for indicator 618. A first position is associated with fluidic connection between the vacuum chamber and the outlet. A second position is associated with fluidic connection between the saline or water chamber and the outlet. A third position is associated with fluidic connection between the air chamber and the outlet. A fourth position is associated with fluidic connection between the side port 618 and the chamber. In an alternative embodiment, there can be a fifth position in which none of the chambers nor the side port 608 are coupled to the outlet. In that embodiment, when the chamber cap 614 is in the fifth position then there is merely a blind cavity behind cap 610.

Figure 9:
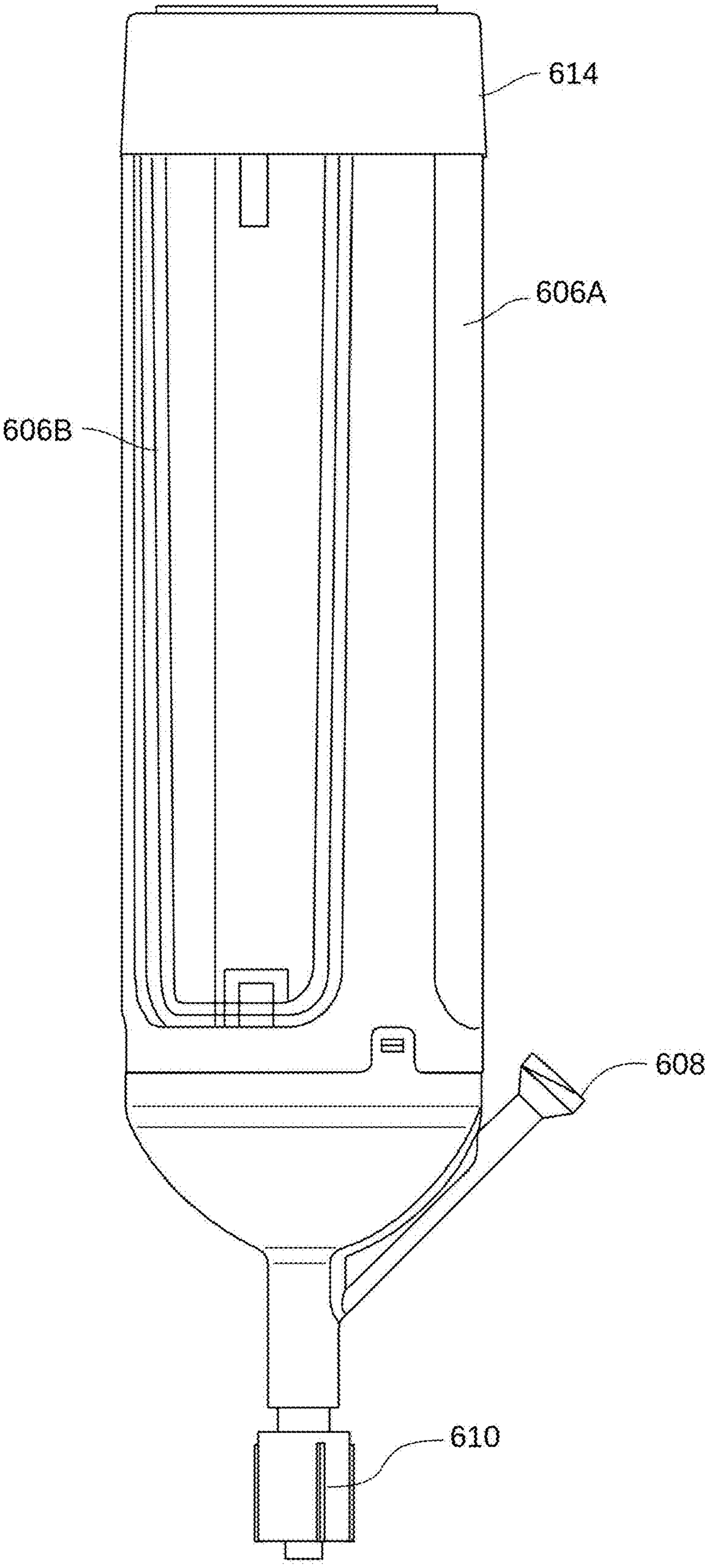
FIG. 9 is a right side view of the multi-fluid rotor of FIG. 6.

FIG. 9 is a side view of the multi-fluid system 600 of FIGS. 6-8. The side views will vary only from one another in that the side port 608 is only arranged on one side, and in that there are three side panels 606 arranged about the periphery of the system 600. Other minor differences will be apparent to those of skill in the art, such as that the small visible portions of the arrow 616 and indicator 618 will vary depending upon the position of chamber cap 614 in its rotation.

Figure 10:
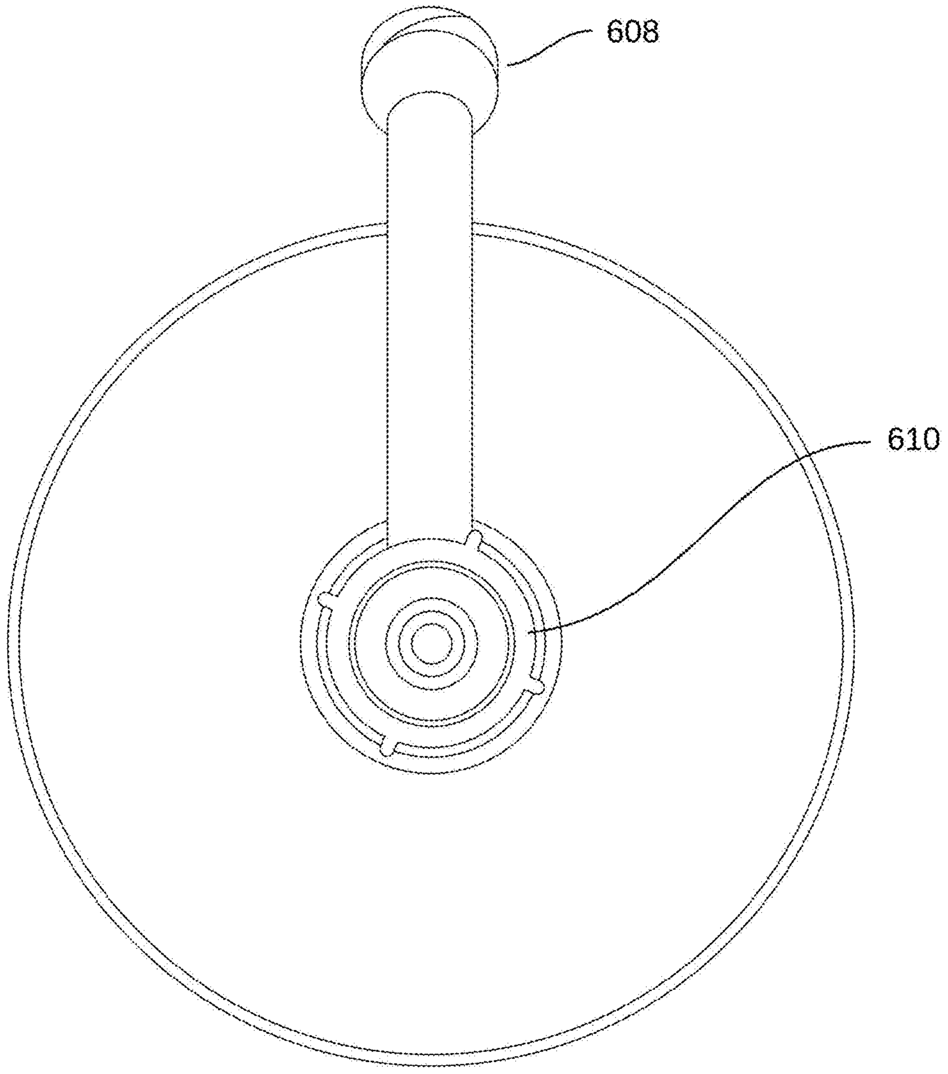
FIG. 10 is a bottom view of the multi-fluid rotor of FIG. 6.

FIG. 10 is a bottom view of multi-fluid system 600 of FIGS. 6-9. FIG. 10 shows side port 608 as well as cap 610.

Figure 11:
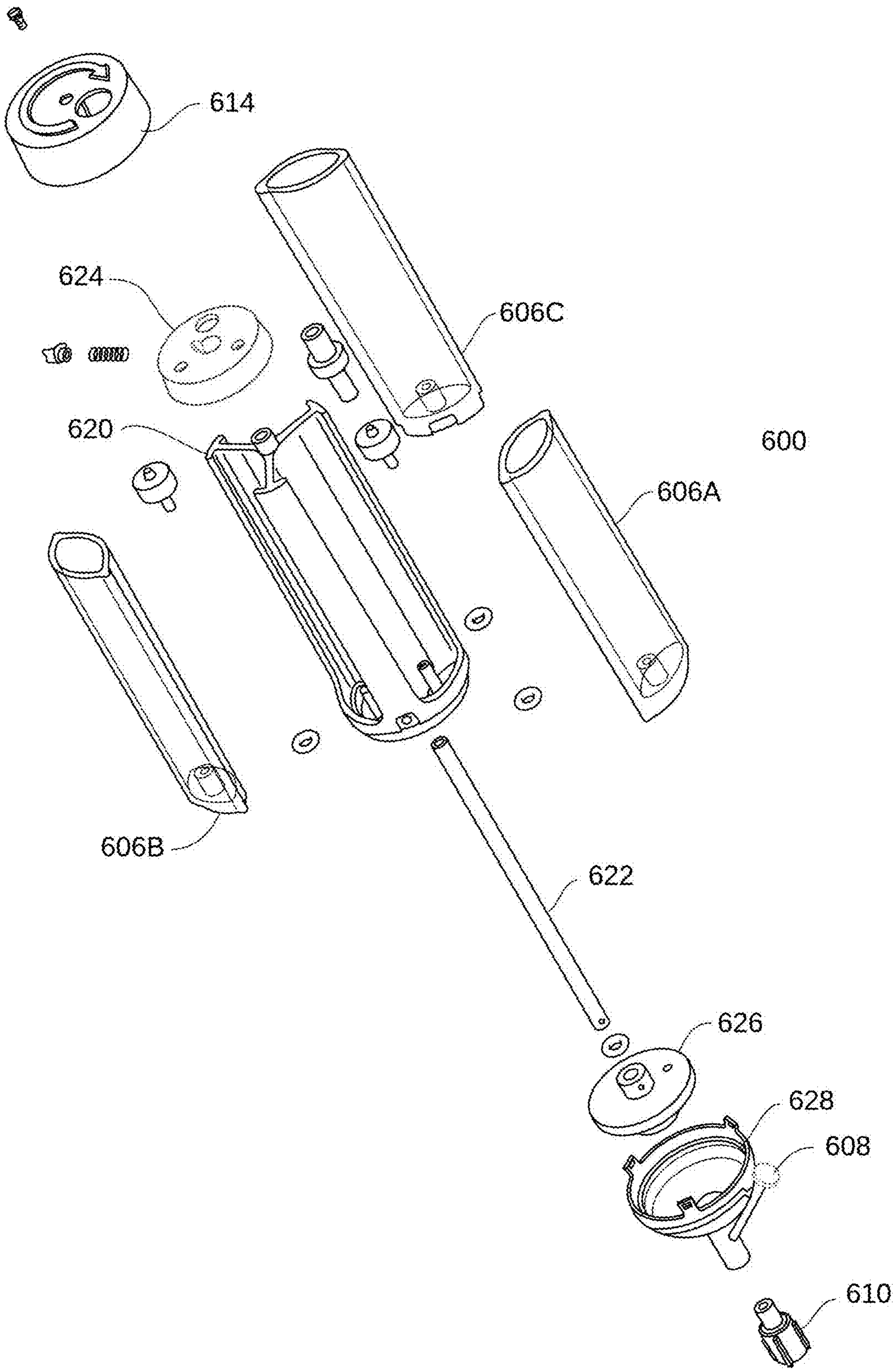
FIG. 11 is an exploded view of a multi-fluid rotor according to an embodiment.

FIG. 11 is an exploded perspective view of multi-fluid system 600 of FIGS. 6-10. FIG. 11 shows the interior components of the system 600, in addition to the external components previously described. System 600 as shown in FIG. 11 includes flexible, compressible side panels 606A, 606B, and 606C. The side panels 606A-606C are selectively fluidically connectable to an outlet aperture at removable cap 610, depending upon the rotational position of chamber cap 614. Chamber cap 614 can be rotated with respect to support 620. When this happens, spindle 622 rotates along with chamber cap 614 due to engagement between spindle 622, hub 624, and chamber cap 614, all of which are configured to co-rotate with respect to the compressible side panels 606A-606C and the support 620.

As spindle 622 rotates with respect to the side panels 606A-606C and support 620, manifold 626 also rotates. Manifold 626 can include one or more fluid channels configured to connect side panels 606A-606C to an outlet. Housing 628 remains stationary with respect to the side panels 606A-606C and the support 620 during rotation of chamber cap 614, and includes the luer outlet and physical support for the other components described above.

As shown in FIG. 11, side port 608 is a part of the housing 628, such that an additional fluid flow channel trough manifold 626 is not required. A skilled artisan will understand that the various gaskets and screws, while not specifically called out with reference numbers herein, are configured to prevent unwanted movement, fluid leakage, or loss of vacuum, such that during use the device 600 can be used to draw and expel samples using vacuum and water or saline, followed by cleaning using air, a wire, or a combination thereof, as described above with respect to FIG. 5.

Figure 12:
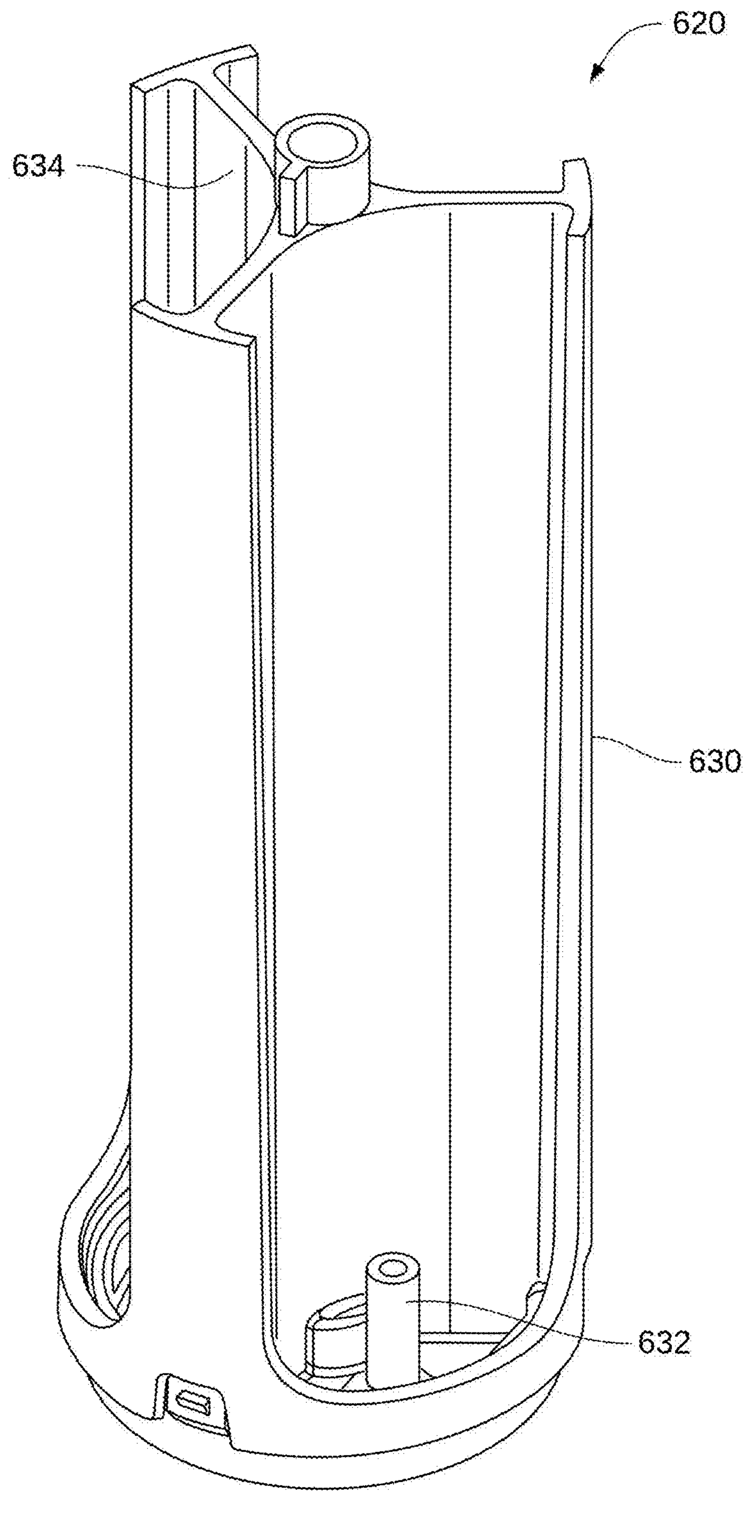
FIG. 12 is a detailed view of a component of the multi-fluid rotor of FIG. 11.

FIG. 12 is a detailed view of support 620. As shown in FIG. 12, support 620 provides space for insertion of the side panels 606A-606C, provides a route for fluid ingress or egress therefrom, and provides increased side panel volume to mass ratio as compared to a support designed to hold cylindrical chambers rather than oblong side panels.

Support 620 of FIG. 12 is made up of arms 630, which are generally "T" shaped, and extend radially outward from the geometric center of support 620. In FIG. 12, there are three such arms 630, though it should be understood that in embodiments there may be more or fewer depending on the desired number of side panels 606A-606C provided, which in turn relates to the number of fluids or vacuum chambers desired. The heads of the "T"s prevent the side panels 606A-606C from shifting or popping out as they are manipulated by a surgeon or other user. Meanwhile, the volume of the support 620 is relatively low, because the trunk of the "T" is relatively small compared to the volume associated with the side panels themselves.

Support 620 of FIG. 12 further includes ports 632, which can include one-way valves, gaskets, or seals as described above in order to create or maintain a desired condition inside a corresponding one of the side panels 606A-606C (i.e., presence of vacuum until rotation of the chamber cap 614 to a predetermined position, or presence of sterile saline or air until squeezed and the rotation of the chamber cap 614 to a predetermined position).

Figure 13:
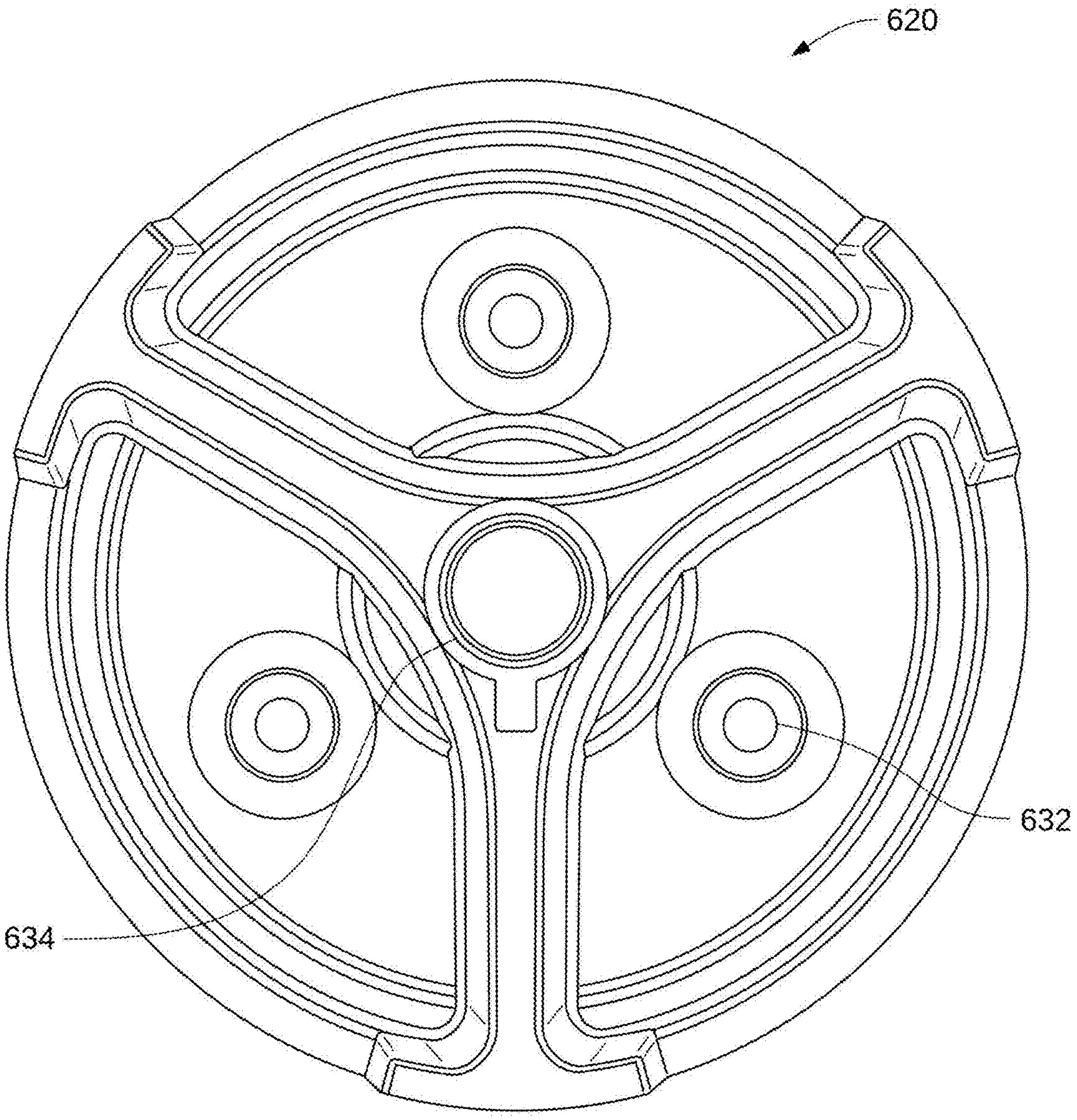
FIG. 13 is a top view of the component of the multi-fluid rotor of FIG. 12.
Figure 14:
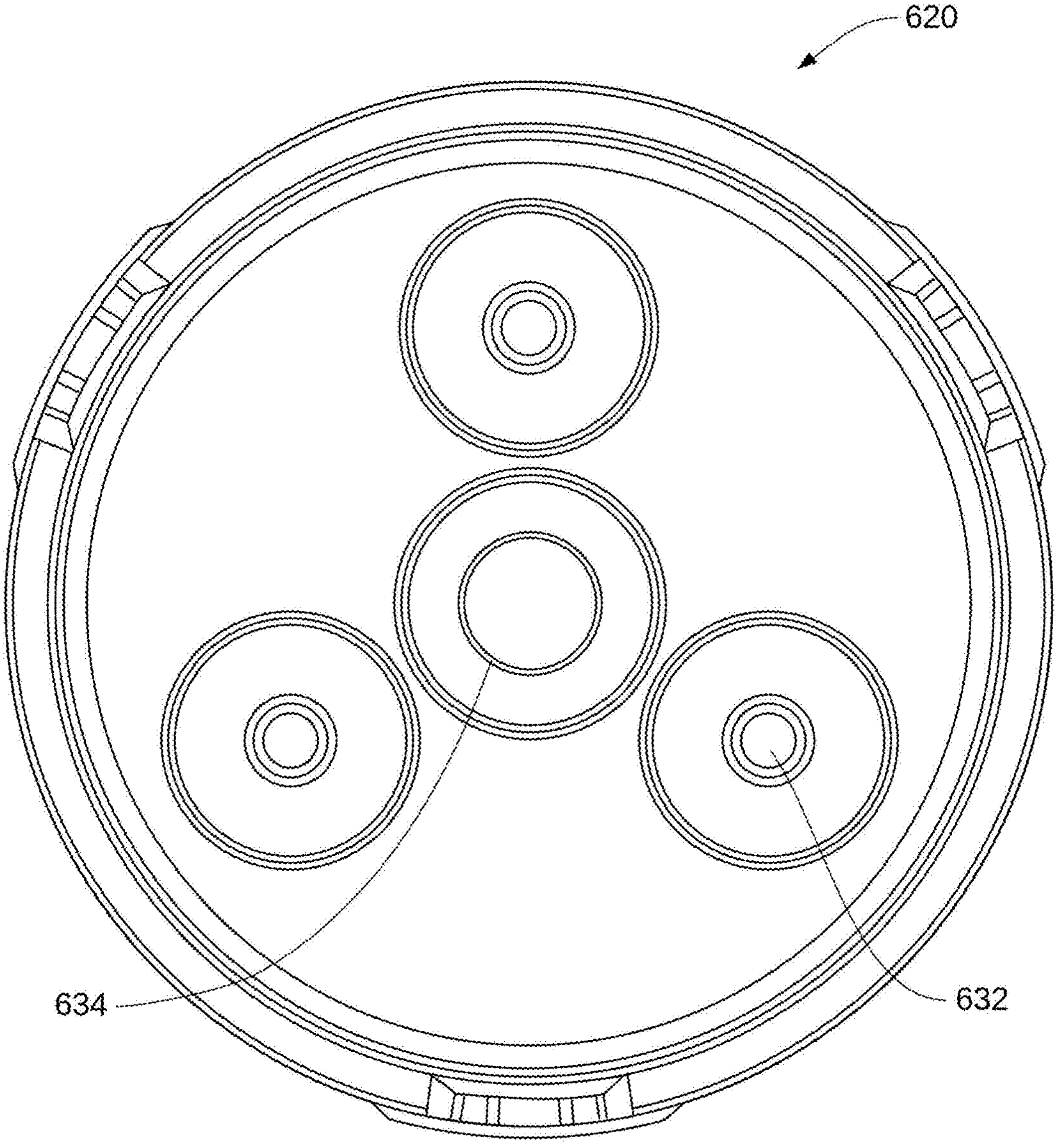
FIG. 14 is a bottom view of the component of the multi-fluid rotor of FIG. 12.

Support 620 of FIG. 12 further includes central bore 634 that is substantially hollow and provides for spindle 622 of FIG. 11 to pass therethrough. FIGS. 13 and 14 provide an end views from the top and bottom, respectively, of the support 620, illustrating a circular central bore 634 though, as described above, in embodiments there may be various ratcheting or other failsafe mechanisms in place that prevent movement in an unwanted direction, and those mechanisms could be implemented in the central bore 634 to prevent undesirable movement, such as rotation in a direction that is inconsistent with the method in FIG. 4 or an alternative method or treatment.

Figure 15:
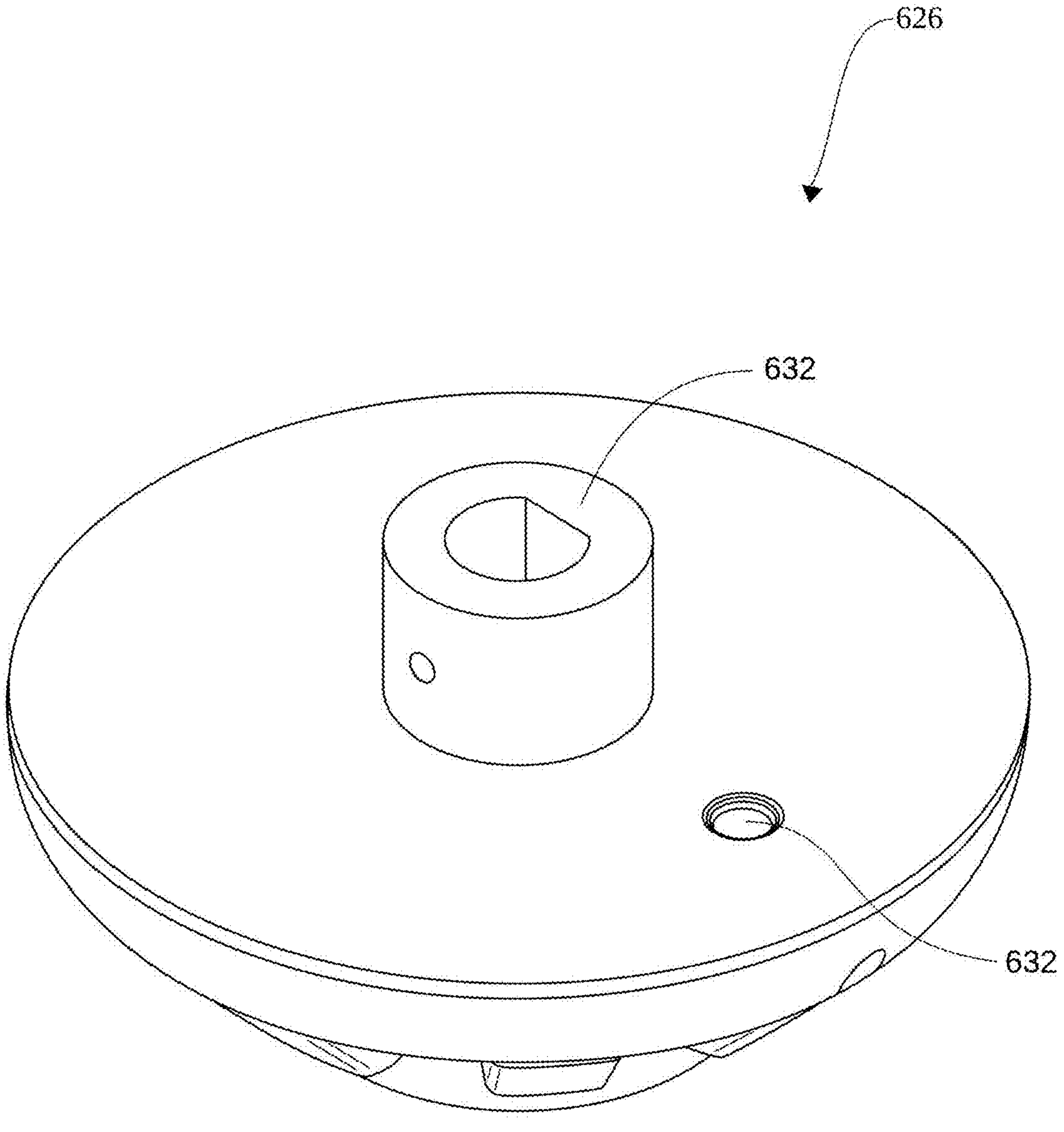
FIG. 15 is a detailed view of a component of the multi-fluid rotor of FIG. 11.
Figure 16:
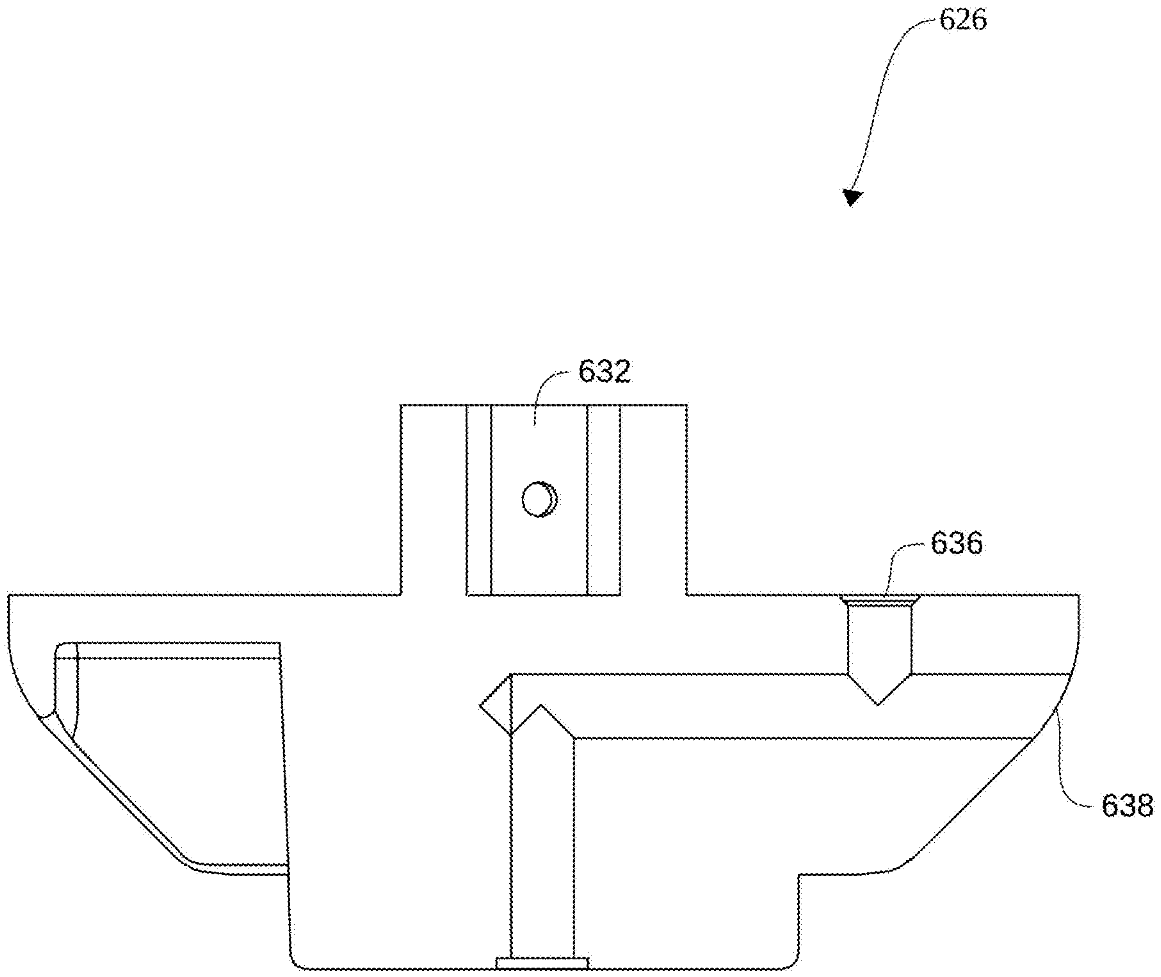
FIG. 16 is a cross-sectional view of the component of the multi-fluid rotor of FIG. 15.

FIG. 15 shows manifold 626, according to an embodiment. As shown in FIG. 15, the manifold 626 includes an aperture 636 that receives the spindle 622 described above. In FIG. 15, the aperture 636 is largely circular except for one flat portion that acts to rotationally lock to a spindle having a corresponding profile. Manifold 626 further includes a fluid aperture 638 that can transmit fluid to or from any of the side panels 606A-606C, depending upon the rotational position of the manifold 626 and whether it is aligned with any one of the side panels 606A-606C. FIG. 16 is a cutaway view showing the interior of manifold 626, which includes both aperture 636 for fluid ingress and egress as well as a second aperture 638 that can be used for routing a fluid, wire, or stopcock as desired.

Figure 17:
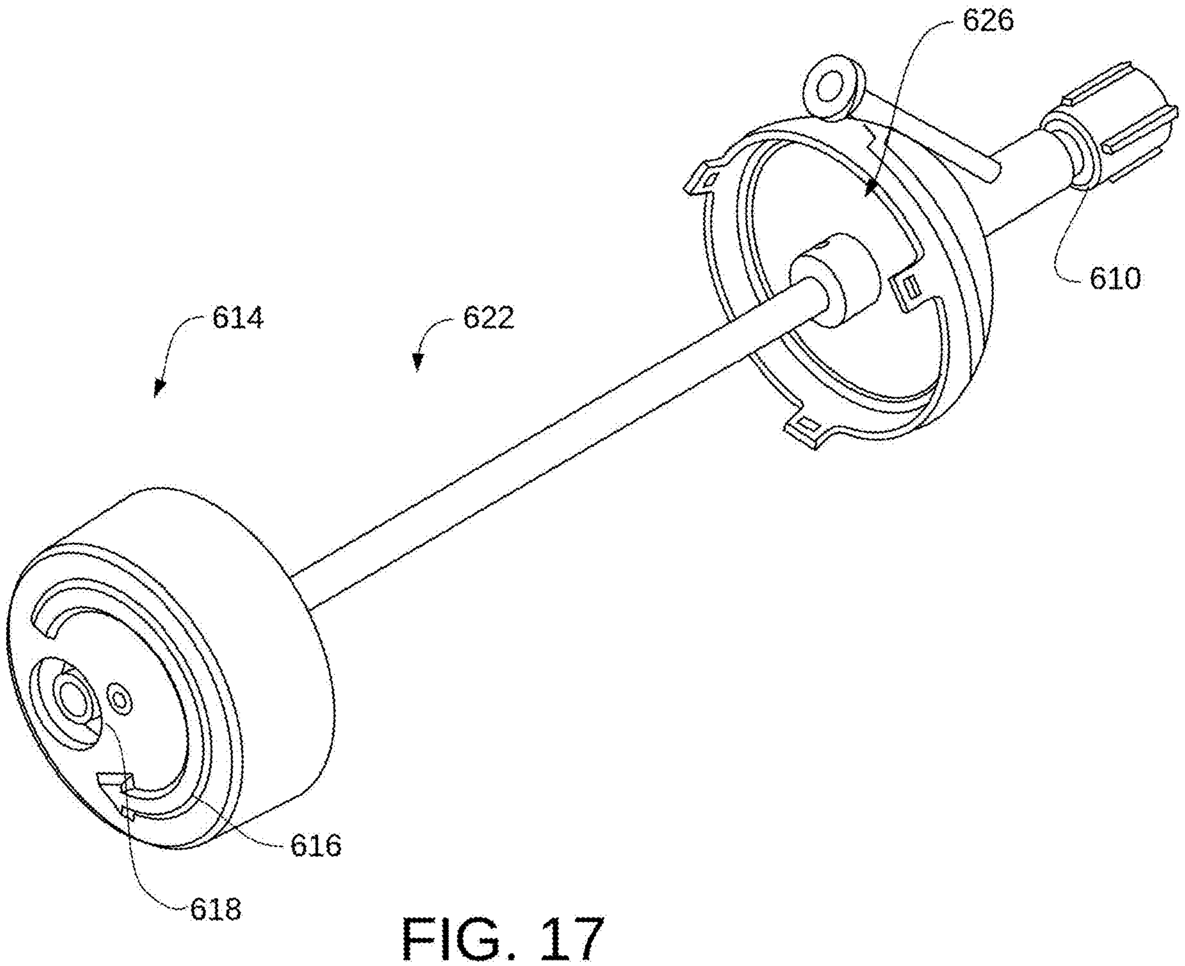
FIG. 17 is a partial perspective view depicting the rotational components of the system of FIG. 6.

FIG. 17 is a cutaway perspective view showing the engagement of spindle 622 between chamber cap 614 and manifold 626. By removing the support 620 and side panels 606A-606C from this view, it is apparent that rotation of the chamber cap 614 as indicated by arrow 616 to a position as indicated by indicator 618 will cause spindle 622 to rotate manifold 626, thus positioning the appropriate fluid reservoir within a side panel 606A-606C in fluid flow contact with the outlet behind cap 610.

Figure 18A:
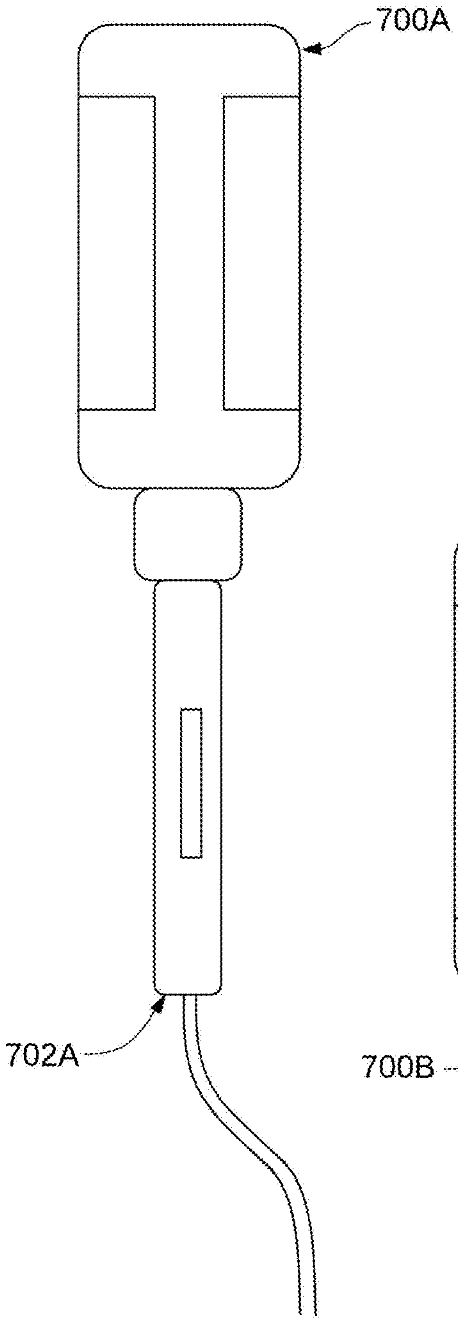
FIGS. 18A, 18B, and 18C are schematic views of three alternative arrangements of a needle and multi-fluid rotor, according to three embodiments.
Figure 18B:
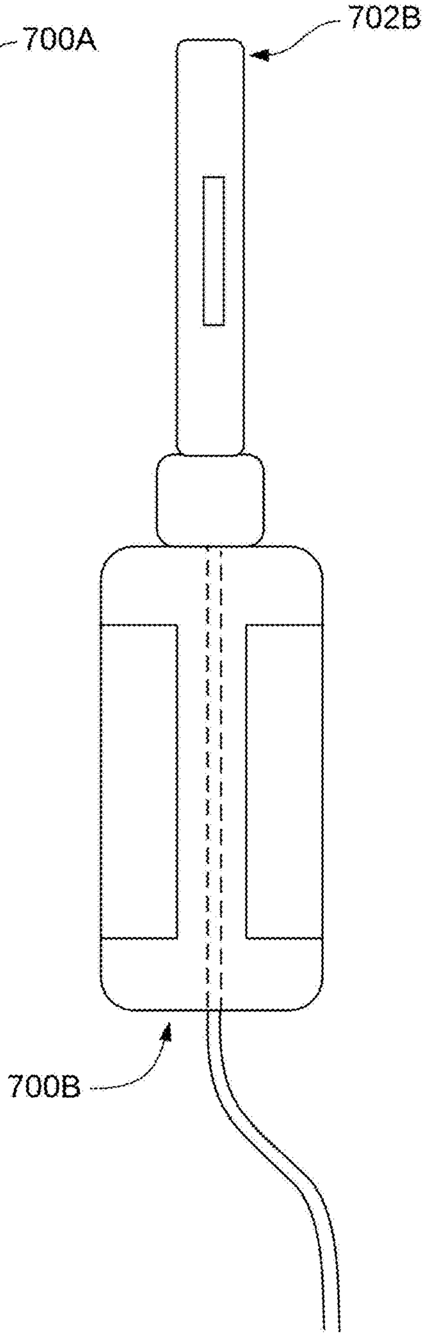
Figure 18C:
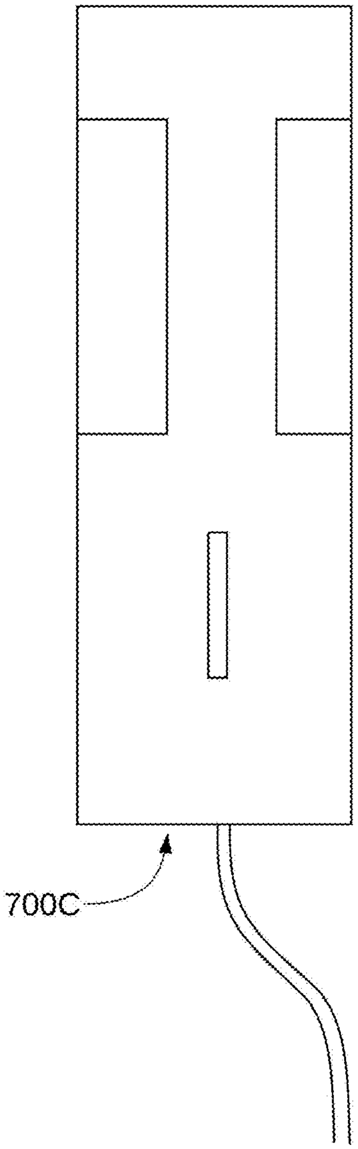

FIGS. 18A-18C depict three alternative embodiments as described above. In the first embodiment shown in FIG. 18A, the multi-fluid system 700A is arranged at the top of a needle 702A, as described above with respect to the embodiments of FIGS. 1-17. In FIG. 18B, the needle 702B is instead arranged atop multi-fluid system 700B, which reduces the mass atop the needle controls and can improve dexterity of the operator in some cases. Finally, FIG. 18C shows an integrated needle control and multi-fluid system 700C, which incorporates both functions rather than connecting the two components as described in other systems.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A multi-chamber syringe module for use with a biopsy needle, the multi-chamber syringe module comprising:

a multi-chamber cartridge having a plurality of fluid chambers and a support that houses the plurality of fluid chambers, each of the plurality of fluid chambers being selectively and temporarily manually deformable to create one of a fluid vacuum therein or a fluid evacuation therefrom, said plurality of fluid chambers forming an exterior wall of the multi-chamber cartridge visible to a user;

a luer fitting hub having a first luer fitting hub end and a second luer fitting hub end, the first luer fitting hub end configured to receive the biopsy needle; and a needle manifold having a first needle manifold end and a second needle manifold end, the first needle manifold end being fixedly coupled with the second luer fitting hub end, and the second needle manifold end being rotatably coupled through a fluid channel to the multi-chamber cartridge to selectively fluidly couple the biopsy needle received in the first luer fitting hub end with one of the plurality of fluid chambers based on a relative rotational arrangement of the needle manifold and the multi-chamber cartridge, said fluid channel including a passage to selectively connect the biopsy needle located on a centerline of the multi-chamber syringe module with the plurality of fluid chambers that are axially offset from the centerline, and wherein said each of the plurality of fluid chambers is configured to enforce a particular order of events.

2. The multi-chamber syringe module of claim 1, wherein the plurality of fluid chambers are selectively removable from the multi-chamber cartridge.

3. The multi-chamber syringe module of claim 1, wherein the plurality of fluid chambers comprise at least one of an elastic material or silicone rubber.

4. The multi-chamber syringe module of claim 1, wherein the plurality of fluid chambers comprise three fluid chambers.

5. The multi-chamber syringe module of claim 4, wherein a first fluid chamber is configured for air evacuation, a second fluid chamber is configured for saline evacuation, and a third fluid chamber is configured as a vacuum.

6. The multi-chamber syringe module of claim 1, wherein a diameter of the multi-chamber syringe module is between about 0.75 inches and about 6 inches.

7. The multi-chamber syringe module of claim 1, wherein a length of the multi-chamber syringe module is between about 4 inches and about 8 inches.

8. The multi-chamber syringe module of claim 1, wherein a volumetric capacity of said each of the plurality of fluid chambers is in a range of about 10 milliliters (mL) to about 30 mL.

9. The multi-chamber syringe module of claim 1, wherein the selective and temporary manual deformation of one of the plurality of fluid chambers applies a negative pressure in a range of about 5 centimeters of water ($cmH_2O$) to about 50 $cmH_2O$.

* * * * *